_United States Patent_ [19]

Miyano et al.

[11] Patent Number: 4,914,227

[45] Date of Patent: Apr. 3, 1990

[54] CERTAIN INTERMEDIATE 3-CARBAMOYLOXYALKYL PROPIOLIC ACID DERIVATIVES

[75] Inventors: Tetsuji Miyano; Kunio Suzuki, both of Nagoya; Nobuo Harada, Okazaki, all of Japan

[73] Assignee: Banyu Pharmaceutical Company, Ltd., Tokyo, Japan

[21] Appl. No.: 863,984

[22] Filed: May 16, 1986

Related U.S. Application Data

[62] Division of Ser. No. 517,844, Jul. 27, 1983, abandoned.

[30] Foreign Application Priority Data

Aug. 6, 1982 [JP] Japan .................................. 57-136343
Sep. 2, 1982 [JP] Japan .................................. 57-151706
Oct. 12, 1982 [JP] Japan .................................. 57-177647

[51] Int. Cl.$^4$ ................. C07C 125/06; C07D 243/06; C07D 413/12
[52] U.S. Cl. ..................................... 560/157; 560/33; 560/32; 560/39; 560/115; 560/159; 548/300; 548/348; 548/352; 548/356; 548/455; 548/465; 548/482; 548/491; 548/518; 548/568; 546/153; 546/157; 546/175; 546/190; 546/193; 546/194; 546/201; 546/205; 546/210; 546/211; 546/233; 546/247; 546/261; 546/273; 546/278; 546/279; 546/281; 546/284; 540/544; 540/575; 544/121; 544/124; 544/128; 544/130; 544/131; 544/139; 544/140; 544/141; 544/143; 544/162; 544/165; 544/168; 544/357; 544/360; 544/370; 544/371; 544/372; 544/400
[58] Field of Search .................. 560/33, 39, 115, 157, 560/159; 546/291, 175, 261, 273, 278, 279, 281, 153, 157, 190, 193, 194, 201, 205, 210, 211, 233, 284, 247; 544/128, 130, 131, 121, 128, 124, 139, 140, 141, 143, 162, 165, 168, 357, 360, 370, 371, 372, 400; 540/544, 575; 548/300, 348, 352, 356, 455, 465, 482, 491, 518, 568

[56] References Cited

U.S. PATENT DOCUMENTS 4,739,106 4/1988 Miyano et al. ...................... 540/575

_Primary Examiner_—Alan L. Rotman
_Attorney, Agent, or Firm_—Oblon, Spivak, McClelland, Maier & Neustadt

[57] ABSTRACT

A process for preparing a 2-carbamoyloxyalkyl-1,4-dihydropyridine derivative represented by the general formula:

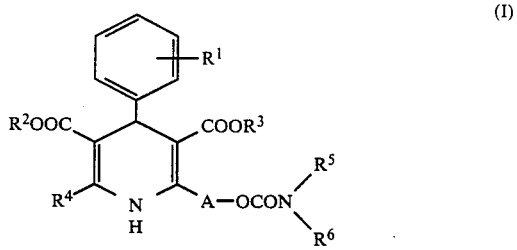

which comprises:
(a) reacting a 3-amino-3-carbamoyloxyalkylacrylic acid derivative represented by the general formula:

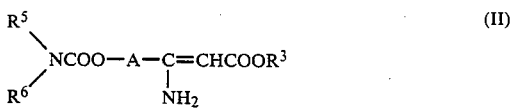

with a benzylidene compound represented by the general formula:

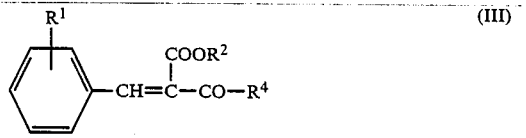

(b) reacting the 3-amino-3-carbamoyloxyalkylacrylic acid derivative of the general formula II with an aldehyde compound represented by the general formula:

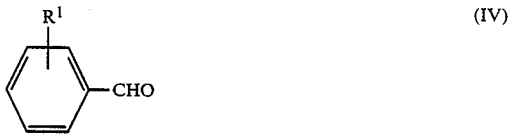

and a β-keto-ester compound represented by the general formula:

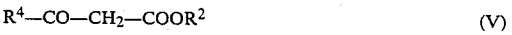

(c) reacting a 3-carbamoyloxyalkylpropiolic acid derivative represented by the general formula:

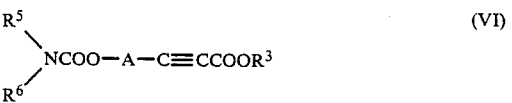

with the benzylidene compound of the general formula III and ammonia or its salt; or
(d) reacting the 3-carbamoyloxyalkylpropiolic acid derivative of the general formula VI with the aldehyde compound of the general formula IV, the β-keto-ester compound of the general formula V and ammonia or its salt.

7 Claims, No Drawings

CERTAIN INTERMEDIATE 3-CARBAMOYLOXYALKYL PROPIOLIC ACID DERIVATIVES

This is a division of application Ser. No. 517,844, filed July 27, 1983, now abandoned.

BACKGROUND OF THE INVENTION

1. Field of the Invention

The present invention relates to a process for preparing 2-carbamoyloxyalkyl-1,4-dihydropyridine derivatives and intermediates useful for the process. More particularly, the present invention relates to a process for the preparation of 2-carbamoyloxyalkyl-1,4-dihydropyridine derivatives which have pharmacological activities, and novel 3-amino-3-carbamoyloxyalkylacrylic acid derivatives and 3-carbamoyloxyalkylpropiolic acid derivatives which are useful as intermediates for the preparation of the dihydropyridine derivatives.

2. Discussion of the Background

2-Carbamoyloxyalkyl-1,4-dihydropyridine derivatives which have substituents with asymmetric structures at 2- and 6-positions of the dihydropyridine ring, are disclosed in Japanese Unexamined Patent Publications No. 118,565/1982 and No. 175,166/1982 by the present inventors. The dihydropyridine derivatives have coronary vasodilation activities or hypotensive activities and are expected to be useful as medicines for the treatment of disorders of circulatory organs.

Processes for the preparation of such asymmetric 1,4-dihydropyridine derivatives have been proposed in which 4-substituted acetoacetic acid esters, 4-substituted-2-ylideneacetoacetic acid esters or 4-substituted-3-aminocrotonic acid esters are used as the starting materials (Japanese Unexamined Patent Publications No. 5,777/1977 and No. 79,873/1978). However, these processes are not so efficient in that they involve a plurality of process steps to prepare the final products, i.e. the asymmetric 1,4-dihydropyridine derivatives, from the respective starting materials.

SUMMARY OF THE INVENTION

As a result of extensive researches, the present inventors have been successful in the preparation of novel 3-amino-3-carbamoyloxyalkylacrylic acid derivatives and 3-carbamoyloxalkylpropiolic acid derivatives which are useful as intermediates or starting materials for the preparation of the asymmetric 1,4-dihydropyridine derivatives. It has been found that with use of these novel intermediates as the starting materials, the asymmetric 1,4-dihydropyridine derivatives can readily be prepared in a single step reaction.

DETAILED DESCRIPTION OF THE PREFERRED EMBODIMENTS

Thus, the present invention provides a process for preparing a 2-carbamoyloxyalkyl-1,4-dihydropyridine derivative represented by the general formula:

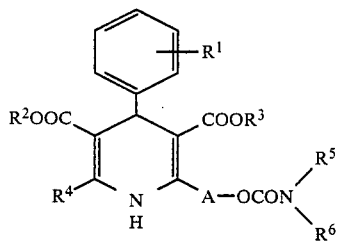
(I)

where $R^1$ is halogen, cyano, nitro, hydroxyl, di-lower alkyl substituted amino or lower alkoxy, each of $R^2$ and $R^3$ is lower alkyl, haloalkyl, lower alkenyl, lower alkynyl, aralkyl, aryl, hydroxyalkyl, lower alkoxyalkyl, lower alkenyloxyalkyl, aralkyloxyalkyl, aryloxyalkyl or

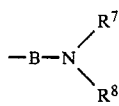

(where B is straight-chained or branched alkylene, and each of $R^7$ and $R^8$ is lower alkyl, aralkyl or aryl, or $R^7$ and $R^8$ form, together with the adjacent nitrogen atom, a heterocyclic group), $R^4$ is hydrogen or lower alkyl, A is alkylene, and each of $R^5$ and $R^6$ is hydrogen, lower alkyl, haloalkyl, hydroxyalkyl, cycloalkyl, aralkyl or aryl, or $R^5$ and $R^6$ form, together with the adjacent nitrogen atom, a heterocyclic group, which comprises:

(a) reacting a 3-amino-3-carbamoyloxyalkylacrylic acid derivative represented by the general formula:

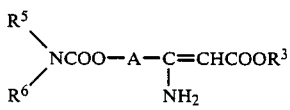
(II)

where $R^3$, $R^5$, $R^6$ and A are as defined above, with a benzylidene compound represented by the general formula:

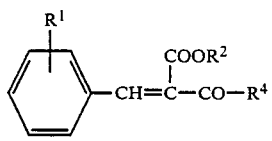
(III)

where $R^1$, $R^2$ and $R^4$ are as defined above;

(b) reacting the 3-amino-3-carbamoyloxyalkylacrylic acid derivative of the general formula II with an aldehyde compound represented by the general formula:

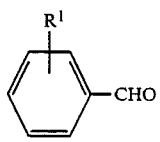
(IV)

where $R^1$ is as defined above, and a β-keto-ester compound represented by the general formula:

$$R^4\text{—}CO\text{—}CH_2\text{—}COOR^2 \tag{V}$$

where $R^2$ and $R^4$ are as defined above;

(c) reacting a 3-carbamoyloxyalkylpropiolic acid derivative represented by the general formula:

$$\begin{array}{c} R^5 \\ \phantom{R^6}\diagdown \\ \phantom{R^6}\phantom{x}NCOO\text{—}A\text{—}C\equiv CCOOR^3 \\ \phantom{R^6}\diagup \\ R^6 \end{array} \tag{VI}$$

where $R^3$, $R^5$, $R^6$ and A are as defined above, with the benzylidene compound of the general formula III and ammonia or its salt; or (d) reacting the 3-carbamoyloxyalkylpropiolic acid derivative of the general formula VI with the aldehyde compound of the general formula IV, the β-keto-ester compound of the general formula V and ammonia or its salt.

The 3-amino-3-carbamoyloxyalkylacrylic acid derivative of the general formula II and the 3-carbamoyloxyalkylpropiolic acid derivative of the general formula VI used as starting materials in the above process, are novel compounds of the present invention.

The 3-amino-3-carbamoyloxyalkylacrylic acid derivative of the general formula II can be prepared by reacting the 3-carbamoyloxyalkylpropiolic acid derivative of the general formula VI with ammonia or its salt.

The 3-carbamoyloxyalkylpropiolic acid derivative of the general formula VI can be prepared by:

(a) reacting an acetylene compound represented by the general formula:

$$HO\text{—}A\text{—}C\equiv CCOOR^3 \tag{VII}$$

where $R^3$ and A are as defined above, with an isocyanate represented by the general formula:

$$R^9NCO$$

where $R^9$ is chlorosulfonyl, dichlorophosphoryl, trichloroacetyl, hydrogen, lower alkyl, cycloalkyl, lower alkenyl, aralkyl or aryl, or a compound capable of forming the isocyanate under the reaction condition, followed by hydrolysis, if necessary, or with a carbamic acid chloride represented by the general formula:

$$\begin{array}{c} R^5 \\ \phantom{R^6}\diagdown \\ \phantom{R^6}\phantom{x}NCOCl \\ \phantom{R^6}\diagup \\ R^6 \end{array}$$

where $R^5$ and $R^6$ are as defined above but excluding hydrogen;

(b) reacting the acetylene compound of the general formula VII with phosgene or trichloromethylchloroformate to form a chloroformic acid ester derivative represented by the general formula:

$$ClCOO\text{—}A\text{—}C\equiv CCOOR^3 \tag{VIII}$$

where $R^3$ and A are as defined above, which is then reacted with an amine compound represented by the general formula:

$$\begin{array}{c} R^5 \\ \phantom{R^6}\diagdown \\ \phantom{R^6}\phantom{x}NH \\ \phantom{R^6}\diagup \\ R^6 \end{array}$$

where $R^5$ and $R^6$ are as defined above; or (c) reacting an acetylene compound represented by the general formula:

$$HO\text{—}A\text{—}C\equiv CH \tag{IX}$$

where A is as defined above, with phosgene or trichloromethylchloroformate to form a chloroformic acid ester derivative represented by the general formula:

$$ClCOO\text{—}A\text{—}C\equiv CH \tag{X}$$

where A is as defined above, which is then reacted with an amine compound represented by the general formula:

$$\begin{array}{c} R^5 \\ \phantom{R^6}\diagdown \\ \phantom{R^6}\phantom{x}NH \\ \phantom{R^6}\diagup \\ R^6 \end{array}$$

where $R^5$ and $R^6$ are as defined above, to form a carbamate derivative represented by the general formula:

$$\begin{array}{c} R^5 \\ \phantom{R^6}\diagdown \\ \phantom{R^6}\phantom{x}NCOO\text{—}A\text{—}C\equiv CH \\ \phantom{R^6}\diagup \\ R^6 \end{array} \tag{XI}$$

where $R^5$, $R^6$ and A are as defined above, which is in turn reacted with a metallizing agent to form an organic metal compound, which is in turn reacted with a chloroformate represented by the general formula:

$$ClCOOR^3$$

where $R^3$ is as defined above.

Now, the present invention will be described in detail with reference to the preferred embodiments.

$R^1$ is halogen such as fluorine, chlorine, bromine or iodine; cyano; nitro; hydroxyl; di-substituted amino such as dimethylamino, diethylamino or dipropylamino; lower alkoxy such as methoxy, ethoxy, propoxy or butoxy.

Each of $R^2$ and $R^3$ is lower alkyl such as methyl, ethyl, propyl, isopropyl, butyl, isobutyl, tertiary butyl, pentyl or hexyl; haloalkyl such as β-chloroethyl, β-bromoethyl, β-chloropropyl, γ-chloropropyl, ω-chlorobutyl, β,β-dichloroethyl, trifluoromethyl or β,β,β-trichloroethyl; lower alkenyl such as vinyl, allyl, 3-butenyl or isopropenyl; lower alkynyl such as propargyl or 2-butynyl; aralkyl such as benzyl, α-methylbenzyl or phenethyl; aryl such as phenyl, pyridyl, naphthyl or quinolyl; hydroxyalkyl such as β-hydroxyethyl, β- hydroxypropyl, β-hydroxybutyl, γ-hydroxypropyl, ω-hydroxybutyl or β,γ-dihydroxypropyl; lower alkoxyalkyl such as β-methoxyethyl, β-ethoxyethyl, β-propoxyethyl, β-isopropoxyethyl, β-butoxyethyl, β-isobutoxyethyl, β-tertiary-butoxyethyl, β-methoxypropyl, β-ethoxypropy, β-propoxypropyl, β-isopropoxypropyl, β-butoxypropyl, γ-methoxypropyl, γ-ethoxypropyl, γ-propoxypropyl, γ-butoxypropyl or ω-propoxybutyl; lower alkenyloxyalkyl such as β-vinyloxyethyl, β-allyloxyethyl, β-(3-butenyloxy)ethyl, β-isopropenyloxyethyl or β-allyloxypropyl; aralkyloxyalkyl such as β-benzyloxyethyl, β-phenethyloxyethyl or β-(α-methylbenzyloxy)ethyl; aryloxyalkyl such as β-phenoxyethyl, β-pyridyloxyethyl, β-phenoxypropyl or β-phenoxybutyl;

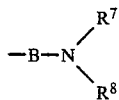

such as β-dimethylaminoethyl, β-diethylaminoethyl, β-methylethylaminoethyl, β-dimethylaminopropyl, γ-dimethylaminopropyl, ω-dimethylaminobutyl, β-N-methylbenzylaminoethyl, β-N-methylbenzylaminopropyl, β-N-methylbenzylaminobutyl, γ-N-methylbenzylaminopropyl, ω-N-methylbenzylaminobutyl, β-piperidinoethyl, β-(4-methylpiperazino)ethyl, β-(4-ethylpiperazino)ethyl, β-(4-propylpiperazino)ethyl, β-(4-methylhomopiperazino)ethyl, β-morpholinoethyl, γ-morpholinopropyl, ω-morpholinobutyl, β-homomorpholinoethyl, β-(1-pyrrolidinyl)ethyl, β-(1-imidazolidinyl)ethyl, β-(1-imidazolinyl)ethyl, β-(1-pyrazolidinyl)ethyl, β-(1-indolinyl)ethyl, β-(2-isoindolinyl)ethyl, or β-N-methylanilinoethyl.

$R^4$ is hydrogen; or lower alkyl such as methyl, ethyl, propyl, isopropyl, butyl, isobutyl or tertiary butyl.

A is alkylene such as methylene, methylmethylene, ethylmethylene, phenylmethylene, dimethylmethylene, methylethylenemethylene, methylisobutylmethylene, phenylmethylmethylene, ethylene, methylethylene, ethylethylene, trimethylene or tetramethylene.

Each of $R^5$ and $R^6$ is hydrogen; lower alkyl such as methyl, ethyl, propyl, isopropyl, butyl, isobutyl or tertiarybutyl; haloalkyl such as β-chloroethyl, β-bromoethyl, β-chloropropyl, γ-chloropropyl, ω-chlorobutyl, β,β-dichloroethyl, β,β,β-trichloroethyl or trifluoromethyl, hydroxyalkyl such as β-hydroxyethyl, β-hydroxypropyl, γ-hydroxypropyl or ω-hydroxybutyl; cycloalkyl such as cyclopropyl, cyclobutyl, cyclopentyl cyclohexyl or cycloheptyl; lower alkenyl such as vinyl, allyl, 3-butenyl or isopropenyl; aralkyl such as benzyl, α-methylbenzyl or phenethyl; aryl such as phenyl, pyridyl or naphthyl, or $R^5$ and $R^6$ form, together with the adjacent nitrogen atom, a heterocyclic group such as piperidino, 4-methylpiperazino, 4-ethylpiperazino, 4-propylpiperazino, 4-methylhomopiperazino, morpholino, homomorpholino, 1-pyrrolidinyl, 1-imidazolidinyl, 1-imidazolinyl, 1-pyrazolidinyl, 1-indolinyl or 2-isoindolinyl.

The aromatic rings contained in the aralkyl, aryl, aralkyloxyalkyl, and aryloxyalkyl of $R^2$ to $R^8$ may be substituted by 1 to 3 substituents. As such substituents, there may be mentioned halogen such as fluorine, chlorine, bromine or iodine, cyano; nitro; hydroxy; di-substituted amino such as dimethylamino, diethylamino or diisopropylamino; lower alkoxy such as methoxy, ethoxy, propoxy or butoxy; lower alkyl such as methyl, ethyl, propyl or butyl; and trifluoromethyl.

Now, the process for the preparation of the 2-carbamoyloxyalkyl-1,4-dihydropyridine derivatives of the general formula I will be specifically described.

In a preferred embodiment of this process, $R^5$ is hydrogen and $R^6$ is hydrogen, lower alkyl, cycloalkyl, lower alkenyl, aralkyl or aryl, $R^1$ to $R^4$ and A being as defined above with respect to the general formula I. More specifically, it is preferred that $R^1$ is o-nitro, m-nitro, o-chloro, o-cyano or o-methoxy, each of $R^2$ and $R^3$ is methyl, ethyl, propyl, isopropyl, butyl, isobutyl, β-chloroethyl, allyl, propargyl, benzyl, phenyl, β-methoxyethyl, β-ethoxyethyl, β-propoxyethyl, β-isopropoxyethyl, β-allyloxyethyl, β-benzyloxyethyl, β-phnoxyethyl, β-N-methylbenzylaminoethyl, β-piperidinoethyl, β-(4-methylpiperazino)ethyl or β-morpholinoethyl, $R^4$ is methyl or ethyl, A is methylene or ethylene, $R^5$ is hydrogen and $R^6$ is hydrogen, methyl, ethyl, propyl, cyclohexyl, phenyl, p-chlorophenyl or m,p-dichlorophenyl.

Among the four methods (a), (b), (c) and (d), the methods (a) and (c) are particularly preferred.

Referring to the methods (a) and (b), the compound of the general formula I is obtained by reacting a 3-amino-3-carbamoyloxyalkylacrylic acid derivative of the general formula II (hereinafter sometimes referred to simply as "an enamine compound") with the benzylidene compound of the general formula III (method (a)) or with the aldehyde compound of the general formula IV and the β-keto-ester compound of the general formula V (method (b)).

The reaction conditions for the methods (a) and (b) are suitably selected depending upon the particular types of the starting materials to be used. In general, the benzylidene compound of the general formula III, or the aldehyde compound of the general formula IV and the β-keto-ester compound of the general formula V, are used substantially in stoichiometric amounts, i.e. equimolar amounts, relative to the enamine compound of the general formula II. The molar ratio of the reactants can be varied within a wide range without adversely affecting the reaction.

The reaction is usually carried out under cooling, at room temperature, or under warming or heating.

As the solvent for the reaction, there may be used water, an inert organic solvent or a solvent mixture of water with an inert organic solvent. As the inert organic solvent, there may be used an alcohol such as methanol, ethanol, propanol, isopropanol or butanol, diethyl ether, dioxane, tetrahydrofuran, acetonitrile, acetone, dimethylformamide, ethylacetate, benzene or chloroform.

The reaction may be facilitated by using a catalyst, for example, an acid such as acetic acid, a base such as piperidine or a salt of an acid with a base.

Referring to the methods (c) and (d), the compound of the general formula I is prepared by reacting a 3-carbamoyloxyalkylpropiolic acid derivative of the general formula VI (hereinafter sometimes referred to simply as "an acetylene compound") with the benzylidene compound of the general formula III and ammonia or its salt, or with the aldehyde compound of the general formula IV, the β-keto-ester compound of the general formula V and ammonia or its salt.

The reaction conditions for the methods (c) and (d) are optionally selected depending upon the particular types of the starting materials to be used. In general, the acetylene compound of the general formula VI, the benzylidene compound of the general formula III, the aldehyde compound of the general formula IV and the β-keto-ester of the general formula V are used substantially in stoichiometric amounts, i.e. equimolar amounts, in the respective reactions, and the ammonia or its salt is used in a stoichiometrically excess amount. The molar ratio of the reactants can be varied within a wide range without adversely affecting the reaction.

As the salt of ammonia, there may be used an ammonium salt of an organic acid such as acetic acid, formic acid, citric acid, benzoic acid or phenylacetic acid, or an ammonium salt of an inorganic acid such as carbonic acid, bicarbonic acid or boric acid.

The reaction is usually carried out under cooling, at room temperature or under warming or heating.

The solvent for the reaction may be water, an inert organic solvent or a solvent mixture of water with an inert organic solvent. As the inert organic solvent, there may be used an alcohol such as methanol, ethanol, propanol, isopropanol, or butanol, diethyl ether, dioxane, tetrahydrofuran, acetonitrile, acetone, dimethylformamide, ethylacetate, benzene or chloroform.

The reaction may be facilitated by using a catalyst such as an acid, a base or a salt of an acid with a base.

The compounds of the general formula I thus prepared by the process of the present invention may be refined, isolated or collected by usual methods such as extraction treatment by means of an organic solvent, separation and purification by chromatography by means of a carrier such as silica gel or alumina, or crystallization. Further, in a case where the compounds thus prepared are capable of forming a salt, they may be converted to the respective salts with use of an inorganic acid such as hydrochloric acid or an organic acid such as citric acid.

The compounds of the general formula I obtained by the present invention have vasodilation activities and hypotensive activities. Particularly, they have strong coronary vasodilation activities and extremely weak toxicity, and thus, they are expected to be quite useful as medicines for the treatment of disorders of the circulatory organs, such as hypertension, cardiac insufficiency, angina pectoris, myocardial infarction or intracerebral vascular disorders.

PHARMACOLOGY

Pharmacological and toxicity tests have been conducted with respect to 2-carbamoyloxyalkyl-1,4-dihydropyridine derivatives obtained by the process of the present invention.

1. Test Methods

(a) Coronary vasodilation

According to Langendorff method (O. Langendorff; Pflügers arch. ges. phisiol., 61, 291–332 (1895)), the coronary vasodilation effects were tested using isolated hearts of rabbits. The strength of coronary vasodilation was evaluated by $ICD_{50}(g/ml)$ i.e. the dosage of a sample required to increase the coronary outflow by 50%.

(b) Acute toxicity

Samples were intravenously administered to DM strain male mice (18 to 22 g), and $LD_{50}$ values were obtained according to the up-and-down method.

(c) Coronary effects on dogs

Beagle dogs (13 to 16 kg, ♂) were subjected to thoracotomy under anesthesia with sodium pentobaribital, and a probe was attached to the heart left coronary anterior descending artery of each animal, whereupon the coronary blood flow (CF) was measured by an electromagnetic flowmeter. On the other hand, a probe was attached to the exposed right femoral artery, and the femoral artery blood flow (FAF) was measured by an electromagnetic flowmeter. A canule was inserted to the left femoral artery, and the systemic blood pressure (BP) was bloody measured by a transducer.

The heart rate (HR) was measured by an electrocardiogram.

The sample solution was intravenously injected to the right femoral vein.

The coronary blood flow (CF), the femoral artery blood flow (FAF) and the heart rate (HR) were represented by a % increase upon the injection of each sample as compared with the respective control value upon the injection of a saline.

The systemic blood pressure (BP) was represented by a % decrease as compared with the control.

2. Results

The coronary vasodilation effects on the isolated heart preparations of rabbits and acute toxicity against the mice are shown in Tables I-1(a) and I-1(b). It is seen that the compounds obtained by the present invention exhibit strong coronary vasodilation effects against the coronary vessels. The acute toxicity thereof is as low as 1/6 to 1/17 of the acute toxicity of nifedipine.

The coronary effects against the beagle dogs are shown in Table I-2. It is seen that the five representative compounds obtained by the present invention increase the coronary blood flow (CF) in correspondence with the increase of their doses, and their effectiveness is equivalent to or greater than the nifedipine. It is also seen that the coronary effects are thereby obtainable without substantially decreasing the systemic blood pressure (BP) or without substantially affecting the heart rate (HR). Thus, no excessive load will be given to the heart, which, coupled with the minimized toxicity, makes the compounds obtained by the present invention quite useful coronary vasodilators.

Further, from the results of a separate pharmacological test where 1 to 10 μg/kg of the compounds of Examples I-3, I-26 and I-38 were intravenously administered, it was found that they increased the cerebral blood flow and the peripheral blood flow by from 40 to 50%, thus indicating that the compounds of the present invention are useful also as cerebral vasodilators and peripheral vasodilators.

TABLE I-1

| | | Coronary vasodilation and acute toxicity | |
|---|---|---|---|
| No. | Compounds: | Coronary vasodilation $ICD_{50}$ g/ml | Acute toxicity $LD_{50}$ mg/kg, i.v. |
| | Reference compound: | | |
| | 2,6-Dimethyl-4-(o-nitrophenyl)-3,5-dimethoxy-carbonyl-1,4-dihydropyridine (nifedipine) | $2.9 \times 10^{-7}$ | 11.5 |
| | Compounds of the present invention: | | |
| (1) | 2-Carbamoyloxymethyl-6-methyl-4-(m-nitrophenyl)-3,5-diethoxycarbonyl-1,4-dihydropyridine | $2.4 \times 10^{-7}$ | 207 |
| (2) | 2-N-Methylcarbamoyloxymethyl-6-methyl-4-(m-nitrophenyl)-3,5-diethoxycarbonyl-1,4-dihydropyridine | $3.2 \times 10^{-7}$ | 71 |
| (3) | 2-Carbamoyloxymethyl-6-methyl-4-(m-nitrophenyl)-3,5-dimethoxycarbonyl-1,4-dihydropyridine | $3.6 \times 10^{-7}$ | 167 |
| (4) | 2-N-Methylcarbamoyloxymethyl-6-methyl-4-(m-nitrophenyl)-3,5-dimethoxycarbonyl-1,4-dihyropyridine | $3.6 \times 10^{-7}$ | 84 |
| (5) | 2-Carbamoyloxymethyl-6-methyl-4-(o-nitrophenyl)-3,5-diethoxycarbonyl-1,4-dihydropyridine | $4.8 \times 10^{-7}$ | 104 |
| (6) | 2-N-Methylcarbamoyloxymethyl-6-methyl-4-(o-nitrophenyl)-3,5-diethoxycarbonyl-1,4-dihydropyridine | $4.5 \times 10^{-7}$ | 30 |
| (7) | 2-Carbomoyloxymethyl-6-methyl-4-(m-nitrophenyl)-3-ethoxycarbonyl-5-isopropoxycarbonyl-1,4-dihydropyridine | $2.4 \times 10^{-7}$ | 76 |
| (8) | 2-N-Methylcarbamoyloxymethyl-6-methyl-4-(m-nitrophenyl)-3-ethoxycarbony-5-isopropoxycarbonyl-1,4-dihydropyridine | $2.3 \times 10^{-7}$ | 37 |
| | Reference compound: | | |
| | 2,6-Dimethyl-4-(o-nitrophenyl)-3,5-dimethoxycarbonyl-1,4-dihydropyridine (nifedipine) | $2.2 \times 10^{-7}$ | 11.5 |
| | Compounds of the present invention: | | |
| (9) | 2-Carbamoyloxymethyl-6-methyl-4-(m-nitrophenyl)-3-ethoxycarbonyl-5-(β-propoxyethoxy)carbonyl-1,4-dihydropyridine | $3.4 \times 10^{-7}$ | 136 |
| (10) | 2-Carbamoyloxymethyl-6-methyl-4-(o-nitrophenyl)-3-ethoxycarbonyl-5-(β-propoxyethoxy)carbonyl-1,4-dihydropyridine | $3.0 \times 10^{-7}$ | 84 |
| (11) | 2-Carbamoyloxymethyl-6-methyl-4-(m-nitrophenyl)-5-ethoxycarbonyl-3-(β-propoxyethoxy)carbonyl-1,4-dihydropyridine | $2.5 \times 10^{-7}$ | 123 |
| (12) | 2-Carbamoyloxymethyl-6-methyl-4-(m-nitrophenyl)-3,5-bis[(β-propoxyethoxy)carbonyl]-1,4-dihydropyridine | $1.5 \times 10^{-7}$ | 123 |
| (13) | 2-N-Methylcarbamoyloxymethyl-6-methyl-4-(m-nitrophenyl)-3,5-bis[(β-propoxyethoxy)carbonyl]-1,4-dihydropyridine | $4.0 \times 10^{-8}$ | 104 |
| (14) | 2-N-Cyclohexylcarbamoyloxymethyl-6-methyl-5-ethoxycarbonyl-3-(β-methoxyethoxy)carbonyl-1,4-dihydropyridine | $3.5 \times 10^{-7}$ | 88 |
| (15) | 2-Carbamoyloxymethyl-6-methyl-4-(m-nitrophenyl)-3-methoxycarbonyl-5-(β-N-methylbenzylaminoethoxy)carbonyl-1,4-dihydropyridine | $4.0 \times 10^{-7}$ | >200 |
| (16) | 2-N-Methylcarbamoyloxymethyl-6-methyl-4-(m-nitrophenyl)-3-methoxycarbonyl-5-(β-N-methylbenzylaminoethoxy)carbonyl-1,4-dihydropyridine | $2.5 \times 10^{-7}$ | 146 |
| (17) | 2-Carbamoyloxymethyl-6-methyl-4-(m-nitrophenyl)-3-methoxycarbonyl-5-[β-(4-methyl-1-piperazinyl)ethoxycarbonyl]-1,4-dihydropyridine | $2.0 \times 10^{-6}$ | 68 |
| (18) | 2-Carbamoyloxymethyl-6-methyl-4-(m- | $1.5 \times 10^{-6}$ | >200 |

TABLE I-1-continued

Coronary vasodilation and acute toxicity

| No. | Compounds: | Coronary vasodilation ICD$_{50}$ g/ml | Acute toxicity LD$_{50}$ mg/kg, i.v. |
|---|---|---|---|
| | nitrophenyl)-3-methoxycarbonyl-5-($\beta$-morpholinoethoxy)carbonyl-1,4-dihydropyridine | | |
| (19) | 2-Carbamoyloxymethyl-6-methyl-4-(m-nitrophenyl)-3-($\beta$-propoxyethoxy)carbonyl-5-($\beta$-N-methylbenzylaminoethoxy)carbonyl-1,4-dihydropyridine | $1.8 \times 10^{-7}$ | 168 |
| (20) | 2-Carbamoyloxymethyl-6-methyl-4-(o-chlorophenyl)-3,5-bis[($\beta$-methoxyethoxy)carbonyl] -1,4-dihyropyridine | $3.6 \times 10^{-7}$ | 184 |
| (21) | 2-N-(p-Chlorophenyl)carbamoyloxymethyl-6-methyl-4-(m-nitrophenyl)-3-ethoxycarbonyl-5-isopropoxycarbonyl-1,4-dihydropyidine | $2.8 \times 10^{-7}$ | 83 |
| (22) | 2-N-Phenylcarbamoyloxymethyl-6-methyl-4-(m-nitrophenyl)-3-ethoxycarbonyl-5-isopropoxycarbonyl-1,4-dihydropyridine | $3.3 \times 10^{-7}$ | 80 |

TABLE I-2

| No. | Compound | Dose μg/kg i.v. | CF % increase | FAF % increase | BP % decrease | HR % increase |
|---|---|---|---|---|---|---|
| | Nifedipine | 1 | 10 | −3 | 2 | 0.6 |
| | | 3 | 48 | −4 | 10 | 2 |
| | | 10 | 86 | 10 | 18 | 4 |
| (1) | [structure: 4-(3-nitrophenyl)-1,4-dihydropyridine with C$_2$H$_5$OOC, COOC$_2$H$_5$, CH$_3$, CH$_2$O—CONH$_2$] | 1 | 4 | 7 | 0 | 0 |
| | | 3 | 30 | 10 | 2 | 2 |
| | | 10 | 74 | 24 | 10 | 4 |
| (2) | [structure: 4-(3-nitrophenyl)-1,4-dihydropyridine with n-C$_3$H$_7$OCH$_2$CH$_2$COC, COOCH$_2$CH$_2$O-n-C$_3$H$_7$, CH$_3$, CH$_2$O—CONH$_2$] | 1 | 14 | 13 | 3 | 0 |
| | | 3 | 50 | 25 | 4 | 0 |
| | | 10 | 90 | 65 | 15 | −2 |
| (3) | [structure: 4-(3-nitrophenyl)-1,4-dihydropyridine with n-C$_3$H$_7$OCH$_2$CH$_2$OOC, COOCH$_2$CH$_2$O-n-C$_3$H$_7$, CH$_3$, CH$_2$O—CONH—CH$_3$] | 1 | 12 | 2 | 2 | 0 |
| | | 3 | 51 | 10 | 2 | 0 |
| | | 10 | 95 | 25 | 20 | −5 |

TABLE I-2-continued

| No. | Compound | Dose μg/kg i.v. | CF % increase | FAF % increase | BP % decrease | HR % increase |
|---|---|---|---|---|---|---|
| (4) | 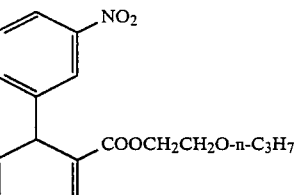 | 1<br>3<br>10 | 13<br>45<br>88 | 13<br>17<br>27 | 0<br>4<br>15 | 0<br>0<br>−3 |
| (5) | 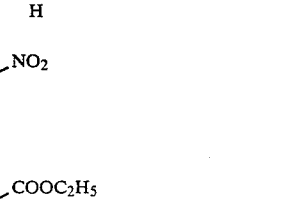 | 1<br>3<br>10 | 13<br>38<br>86 | 8<br>35<br>82 | 0<br>2<br>22 | 0<br>0<br>−10 |

Thus, the compounds of the general formula I obtained by the process of the present invention are expected to be useful as vasodilators as well as hypotensive drugs. The mode of administration of the compounds may be optionally chosen for such a purpose, and it may be e.g. parenteral administration such as intravenous, hypodermic or intramascular injection or rectal administration, or oral administration in a form of tablets, powders, granules, capsules, sublingual tablets or syrups. The dose may vary depending upon the diseased condition, age and weight of the patient and the mode of the administration, but is usually from 0.1 to 1,000 mg per day, preferably from 1 to 100 mg per day, for an adult. The above-mentioned formulations may be prepared by conventional methods which are commonly employed.

Now, the preparation of the novel enamine compounds of the general formula II and acetylene compounds of the general formula VI which are useful as intermediates of the compounds of the general formula I, will be described in detail.

Referring firstly to the process for the preparation of the enamine compound, the 3-amino-3-carbamoyloxyalkylacrylic acid derivatives of the the general formula II (i.e. the enamine compounds) are prepared by reacting a 3-carbamoyloxyalkylpropiolic acid derivative represented by the general formula:

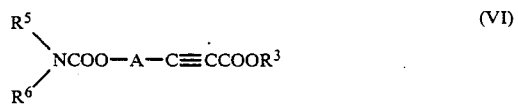

where $R^3$, $R^5$, $R^6$ and A are as defined above, with ammonia or its salt.

The salt of ammonia may be an inorganic ammonium salt such as ammonium carbonate, bicarbonate or borate, or an organic ammonium salt such as ammonium formate, acetate, propionate, butyrate, tartrate, citrate, glutarate, oxalate, benzoate, phenylacetate, salicylate, phthalate or nicotinate.

In this process, ammonia or its salt is usually used in an amount of from 1 to 10 moles, preferably from 1 to 5 moles, per mole of the starting material of the general formula VI.

The reaction is carried out at room temperature or a slightly elevated temperature.

The solvent for the reaction may be selected from a lower alcohol such as methanol, ethanol, propanol, isopropanol, butyl alcohol, isobutyl alcohol, secondary butyl alcohol, tertiary butyl alcohol or amyl alcohol, ethylene glycol, propylene glycol, glycerol, methylcellusolve, ethylene glycol dimethyl ether, dimethylsulfoxide, dimethylformamide, acetone, tetrahydrofuran and acetonitrile. Further, as the solvent for the reaction, a solvent mixture of water with an inert organic solvent such as benzene, ethylacetate, chloroform or diethyl ether may also be used other than the above-mentioned organic solvents.

The reaction time is usually from 1 to 10 hours, preferably from 1 to 5 hours.

In a preferred embodiment, $R^3$ is methyl, ethyl, propyl, isopropyl, butyl, isobutyl, β-chloroethyl, allyl, propargyl, benzyl, phenyl, β-methoxyethyl, β-propoxyethyl, β-isoporpoxyethyl, β-allyloxyethyl, β-benzyloxyethyl, β-phenoxyethyl, β-N-methylbenzylaminoethyl, β-piperidinoethyl, β-(4-methylpiperazino)ethyl, or β-morpholinoethyl, each of $R^5$ and $R^6$ is hydrogen, methyl, ethyl, propyl, isopropyl, butyl, isobutyl, tertiary butyl, β-chloroethyl, benzyl, phenyl, β-chlorophenyl, β-hydroxyethyl or cyclohexyl, or $R^5$ and $R^6$ form, together with the adjacent nitrogen atom a heterocyclic group selected from the group consisting of piperidino, 4-methylpiperazino and morpholino and A is methylene, ethylene, methyl methylene or dimethyl methylene.

Among the enamine compounds of the general formula II thus obtainable, preferred are β-methoxyethyl 3-amino-4-carbamoyloxycrotonate, methyl 3-amino-4-N-methylcarbamoyloxycrotonate, ethyl 3-amino-4-N-methylcarbamoyloxycrotonate, β-methoxyethyl 3-amino-4-N-methylcarbamoyloxycrotonate, ethyl 3-amino-4-N-ethylcarbamoyloxycrotonate, ethyl 3-amino-4-N-propylcarbamoyloxycrotonate, ethyl 3-amino-4-N-t-butylcarbamoyloxycrotonate, ethyl 3-amino-4-N-cyclohexylcarbamoyloxycrotonate, ethyl 3-amino-4-N-phenylcarbamoyloxycrotonate, methyl 3-amino-4-N-(p-chlorophenyl)carbamoyloxycrotonate, β-propoxyethyl 3-amino-4-N,N-dimethylcarbamoyloxycrotonate, ethyl 3-amino-4-N,N-dicyclohexylcarbamoyloxycrotonate, ethyl 3-amino-4-N,N-diphenylcarbamoyloxycrotonate, ethyl 3-amino-4-piperidinocarbonyloxycrotonate, ethyl 3-amino-4-(4-methylpiperazino)carbonyloxycrotonate, ethyl 3-amino-4-morpholinocarbonyloxycrotonate, ethyl 3-amino-4-N,N-bis(β-chloroethyl)carbamoyloxycrotonate, ethyl 3-amino-4-N-benzyl-N-methylcarbamoyloxycrotonate, ethyl 3-amino-4-carbamoyloxycrotonate, isobutyl 3-amino-4-carbamoyloxycrotonate, β-propoxyethyl 3-amino-4-carbamoyloxycrotonate, β-propoxyethyl 3-amino-4-N-methylcarbamoyloxycrotonate, methyl 3-amino-4-carbamoyloxycrotonate and isopropyl 3-amino-4-carbamoyloxycrotonate. Most preferred are methyl 3-amino-4-carbamoyloxycrotonate and isopropyl 3-amino-4-carbamoyloxycrotonate.

Referring now to the process for the preparation of the acetylene compounds of the present invention, the 3-carbamoyloxyalkylpropiolic acid derivatives of the general formula VI (i.e. the acetylene compounds) are prepared by:

(a) reacting an acetylene compound represented by the general formula:

$$HO-A-C\equiv CCOOR^3 \quad (VII)$$

where $R^3$ and A are as defined above, with an isocyanate represented by the general formula:

$$R^9NCO$$

where $R^9$ is chlorosulfonyl, dichlorophosphoryl, trichloroacetyl, hydrogen, lower alkyl, cycloalkyl, lower alkenyl, aralkyl or aryl, or a compound capable of forming the isocyanate under the reaction condition, followed by hydrolysis, if necessary, or with a carbamic acid chloride represented by the general formula:

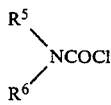

where $R^5$ and $R^6$ are as defined above but excluding hydrogen;

(b) reacting the acetylene compound of the general formula VII with phosgene or trichloromethylchloroformate to form a chloroformic acid ester derivative represented by the general formula:

$$ClCOO-A-C\equiv CCOOR^3 \quad (VIII)$$

where $R^3$ and A are as defined above, which is then reacted with an amine compound represented by the general formula:

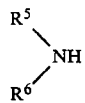

where $R^5$ and $R^6$ are as defined above; or (c) reacting an acetylene compound represented by the general formula:

$$HO-A-C\equiv CH \quad (IX)$$

where A is as defined above, with phosgene or trichloromethylchloroformate to form a chloroformic acid ester derivative represented by the general formula:

$$ClCOO-A-C\equiv CH \quad (X)$$

where A is as defined above, which is then reacted with an amine compound represented by the general formula:

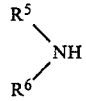

where $R^5$ and $R^6$ are as defined above, to form a carbamate derivative represented by the general formula:

(XI)

where $R^5$, $R^6$ and A are as defined above, which is in turn reacted with a metallizing reagent to form an organic metal compound, which is in turn reacted with a chloroformate represented by the general formula:

$$ClCOOR^3$$

where $R^3$ is as defined above.

The reaction process of the method (a) may be illustrated by the following reaction scheme in a case where ethyl 4-hydroxy-2-butynoate and methyl isocyanate are used as starting materials:

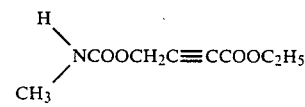

The reaction process of the method (b) may be illustrated by the following reaction scheme in a case where ethyl 4-hydroxy-2-butynoate, phosgene and dimethylamine are used as starting materials:

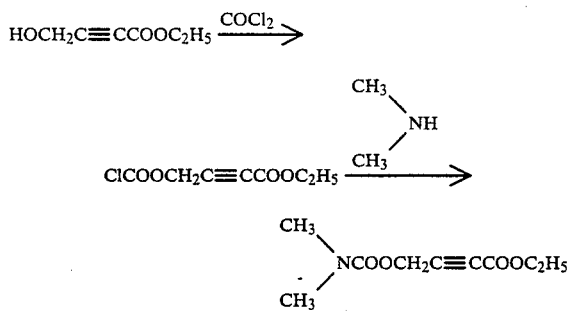

The reaction process of the method (c) may be illustrated by the following reaction scheme in a case where propargyl alcohol, phosgene, dimethylamine, butyl lithium and ethylchloroformate are used as starting materials.

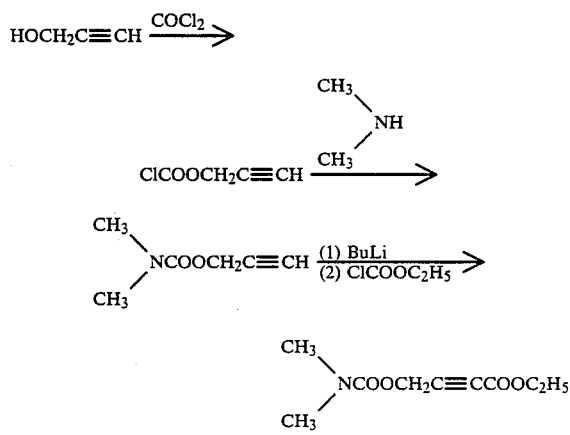

The starting acetylene compounds of the general formulas VII and IX are known compounds or may readily be prepared by known methods if not disclosed in literatures. (M. Mark Midland; J. Org. Chem., 40, 2250–2252 (1975), Henne Greenlee; J. Am. Chem. Soc., 67, 484 (1945)).

The method (a) is concerned with the preparation of the compound of the formula VI by reacting the acetylene compound of the general formula VII with an isocyanate or a carbamic acid chloride.

As the isocyanate of the general formula $R^9NCO$ (where $R^9$ is as defined above), there may be mentioned chlorosulfonyl isocyanate, dichlorophosphoryl isocyanate, trichloroacetyl isocyanate, isocyanic acid, methyl isocyanate, ethyl isocyanate, propyl isocyanate, isopropyl isocyanate, butyl isocyanate, isobutyl isocyanate, tert.-butyl isocyanate, allyl isocyanate, cyclohexyl isocyanate, cyclopentyl isocyanate, phenyl isocyanate, o-, m- or p-chlorophenyl isocyanate, o-, m- or p-nitrophenyl isocyanate, m,p-dichlorophenyl isocyanate, p-fluorophenyl isocyanate, p-methoxyphenyl isocyanate, p-tolyl isocyanate, p-dimethylaminophenyl isocyanate, benzyl isocyanate, diphenylmethyl isocyanate, phenethyl isocyanate or β-dimethylaminoethyl isocyanate.

As the carbamic acid chloride of the general formula

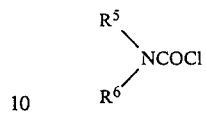

(where $R^5$ and $R^6$ are as defined above) to be used in this method, there may be mentioned dimethylcarbamylchloride, diethylcarbamylchloride, dipropylcarbamylchloride, diisopropylcarbamylchloride, methylethylcarbamylchloride, methylbenzylcarbamylchloride and methylphenylcarbamylchloride.

In this reaction, instead of the isocyanate of the general formula $R^9NCO$, a compound capable of forming such an isocyanate under the reaction condition as mentioned below may be used. As such a compound, there may be mentioned an acid azide represented by the general formula $R^9CON_3$ (where $R^9$ is as defined above) under a heating condition, or a thiocarbamate represented by the general formula $R^9NHCOSR$ (where $R^9$ is as defined above, and R is lower alkyl) under a heating condition or in the presence of a trialkylamine and a heavy metal (for instance, silver nitrate or mercury chloride).

The reaction condition for the method (a) for the preparation of the compound of the general formula VI is suitable selected depending upon the particular types of the starting materials to be used. In general, the isocyanate of the general formula $R^9NCO$ (where $R^9$ is as defined above) or the carbamic acid chloride of the general formula

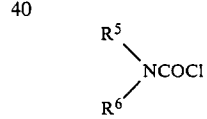

(where $R^5$ and $R^6$ are as defined above) are used in an amount of from 1 to 2 moles per mole of the acetylene compound of the general formula VII. The molar ratio of the starting materials may be varied within a wide range without adversely affecting the reaction. The reaction is usually carried out under cooling, at room temperature or under warming or heating.

In the case where the carbamic acid chloride is employed, a base such as pyridine, triethylamine or dimethylaniline is used in an equimolar amount or in an excess amount relative to the carbamic acid chloride. As the solvent for the reaction, an inert organic solvent such as dichloromethane, chloroform, diethyl ether, tetrahydrofuran or benzene is usually used. The reaction is usually carried out for 1 to 24 hours under stirring.

When chlorosulfonyl isocyanate, dichlorophosphoryl isocyanate or trichloroacetyl isocyanate is used as the isocyanate, it will be necessary to conduct hydrolysis treatment of the reaction mixture by adding water thereto after the completion of the reaction.

Referring now to the method (b), firstly the compound of the general formula VIII is synthesized by the reaction of the acetylene compound of the general formula VII with phosgene or trichloromethylformate, and then the compound of the general formula VI is prepared by the reaction of the compound of the general formula VIII with an amine compound of the general formula

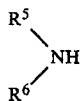

(where $R^5$ and $R^6$ are as defined above). The trichloromethylformate to be used in this reaction is contacted with a very small amount of pyridine or active carbon, whereupon the generated phosgene gas is absorbed in an inert organic solvent such as benzene, or is dropwise added to a solution of an inert organic solvent such as benzene to obtain a phosgene solution, as a pretreating operation before the reaction with the acetylene compound of the general formula VII. As the amine compound of the general formula

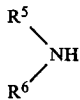

(where $R^5$ and $R^6$ are as defined above) to be used in this reaction, there may be mentioned ammonia, methylamine, ethylamine, propylamine, isopropylamine, butylamine, isobutylamine, tertiary-butylamine, dimethylamine, diethylamine, dipropylamine, diisopropylamine, dibutylamine, diisobutylamine, methylethylamine, diethanolamine, cyclohexylamine, dicyclohexylamine, allylamine, benzylamine, α-methylbenzylamine, phenethylamine, aniline, diphenylamine, α-pyridylamine, α-naphthylamine, N-methylbenzylamine, N-methylaniline, pyperidine, 4-methylpyperazine, 4-methylhomopyperazine, morpholine, homomorpholine, pyrrolidine, imidazolidine, imidazoline, pyrazolidine, indoline and isoindoline.

In the method (b), the reaction condition for the reaction of the acetylene compound VII with phosgene or trichloromethylchloroformate is usually such that phosgene or trichloromethylchloroformate is used in an amount of from 1 to 2 moles per mole of the acetylene compound of the general formula VII.

In the method (b), the reaction condition for the reaction of the compound of the general formula VIII with the amine compound is usually such that relative to one mole of the compound of the general formula VIII, the amine compound of the general formula

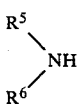

(where $R^5$ and $R^6$ are as defined above) is used in an amount of from 2 to 3 moles, or the amine compound in an amount of from 1 to 2 moles is used in combination with from 1 to 2 moles of a tertiary amine such as triethylamine, dimethylaniline or pyridine.

The molar ratio of the reactants may be varied within a wide range without adversely affecting the reactions. In each case, the reaction is carried out under cooling with ice or at room temperature. In each reaction, an inert organic solvent such as diethyl ether, tetrahydrofuran, benzene, toluene, dichloromethane or chloroform is usually used as the solvent. With respect to the reaction time, each reaction is carried out under stirring for 30 minutes to 3 hours, followed by stirring for one night at room temperature for completion.

The method (c) is a continuous or successive process for the preparation of the compound of the general formula VI in which firstly the compound of the general formula X is prepared by the reaction of the acetylene compound of the general formula IX with phosgene or trichloromethylchloroformate, then the compound of the general formula XI is prepared by the reaction of the compound of the general formula X with the amine compound of the general formula

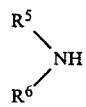

(where $R^5$ and $R^6$ are as defined above, but excluding hydrogen), further a metallizing reagent is reacted to the compound of the general formula XI to form an organic metal compound and then a chloroformate of the general formula $ClCOOR^3$ (where $R^3$ is as defined above) is reacted thereto. As the amine compound of the general formula

(where $R^5$ and $R^6$ are as defined above, but excluding hydrogen), there may be mentioned the amine compounds mentioned in the above method (b), except for ammonia and primary amines such as methylamine and benzylamine. As the chloroformate of the general formula $ClCOOR^3$ (where $R^3$ is as defined above) to be used in the reaction of the method (c), there may be mentioned, methylchloroformate, ethylchloroformate, propylchloroformate, isopropylchloroformate, β-chloroethylchloroformate, allylchloroformate, propargylchloroformate, benzylchloroformate, phenylchloroformate, β-methoxyethylchloroformate, β-ethoxyethylchloroformate, β-propoxyethylchloroformate, β-isopropoxyethylchloroformate, β-butoxyethylchloroformate, β-propoxypropylchloroformate, β-allyloxyethylchloroformate, β-benzyloxyethylchloroformate, β-phenoxyethylchloroformate, β-dimethylaminoethylchloroformate, β-diethylaminoethylchloroformate, β-N-methylbenzylaminoethylchloroformate, β-N-methylbenzylaminopropylchloroformate, β-piperidinoethylchloroformate, β-(4-methylpiperazino)ethylchloroformate, β-morpholinoethylchloroformate, and γ-(4-methylhomopiperazino)propylchloroformate.

As the metallizing reagent to be used for the reaction of the method (c), there may be mentioned methyl lithium, ethyl lithium, n-propyl lithium, n-butyl lithium, s-butyl lithium, t-butyl lithium, cyclopropyl lithium, vinyl lithium, cis-propenyl lithium, phenyl lithium, triphenylmethyl lithium, lithium diisopropylamide, lithium diethylamide, lithium di-trimethylsilylamide, lithium benzylamide, lithium cyclohexylamide, sodium, potassium, lithium, sodium amide, potassium amide, lithium amide, magnesium methyliodide, magnesium ethyliodide, magnesium methylbromide, magnesium ethylbromide and magnesium phenylchloride.

In the method (c), the reactions of the first two steps, i.e. the reaction of the acethylene compound of the general formula IX with phosgene or trichloromethylchloroformate and the reaction of the compound of the general formula X with the amine compound, are conducted in the same manner, with respect to the reaction conditions, reaction temperatures, solvents and reaction times as the corresponding reactions in the above-mentioned method (b).

The reaction of the compound of the general formula XI with the metallizing reagent in the method (c) is usually conducted under such a condition that the metallizing reagent is used in an equtmolar amount or a slightly excess amount relative to the compound for the general formula XI, and the chloroformate is used in an amount of from 1 to 2 moles per mole of the compound. The reaction with the metallizing reagent is conducted under cooling with ice or at a lower temperature to $-120°$ C., preferably from $-60°$ to $-80°$ C., and the reaction with the chloroformate is conducted under cooling with ice or at a lower temperature to $-80°$ C., preferably from $-60°$ to $-80°$ C. As the solvent for the reactions, an inert organic solvent such as diethyl ether or tetrahydrofuran is used. With respect to the reaction time, the reaction with the metallizing reagent is conducted for from 10 to 30 minutes, followed immediately by the reaction with the chloroformate for from 30 to 60 minutes.

In a preferred embodiment, $R^3$ is methyl, ethyl, propyl, isopropyl, butyl, isobutyl, β-chloroethyl, allyl, propargyl, benzyl, phenyl, β-methoxyethyl, β-propoxyethyl, β-isopropoxyethyl, β-allyloxyethyl, β-benzyloxyethyl, β-phenoxyethyl, β-N-methylbenzylaminoethyl, β-piperidinoethyl, β-(4-methylpiperazino)ethyl, or β-morpholinoethyl, each of $R^5$ and $R^6$ is hydrogen, methyl, ethyl, propyl, isopropyl, butyl, isobutyl, tertiary butyl, β-chloroethyl, benzyl, phenyl, β-chlorophenyl, β-hydroxyethyl or cyclohexyl, or $R^5$ and $R^6$ form, together with the adjacent nitrogen atom a heterocyclic group selected from the group consisting of piperidino, 4-methylpiperazino and morpholino and A is methylene, ethylene, methyl methylene or dimethyl methylene.

Among the 3-carbamoyloxyalkylpropiolic acid derivatives of the general formula VI thus obtainable, preferred are methyl 4-carbamoyloxy-2-butynoate, ethyl 4-carbamoyloxy-2-butynoate, isopropyl 4-carbamoyloxy-2-butynoate, isobutyl 4-carbamoyloxy-2-butynoate, β-methoxyethyl 4-carbamoyloxy-2-butynoate, β-propoxyethyl 4-carbamoyloxy-2-butynoate, methyl 4-N-methylcarbamoyloxy-2-butynoate, ethyl 4-N-methylcarbamoyloxy-2-butynoate, β-methoxyethyl 4-N-methylcarbamoyloxy-2-butynoate, β-propoxyethyl 4-N-methylcarbamoyloxy-2-butynoate, ethyl 4-N-ethylcarbamoyloxy-2-butynoate, ethyl 4-N-propylcarbamoyloxy-2-butynoate, ethyl 4-N-t-butylcarbamoyloxy-2-butynoate, ethyl 4-N-cyclohexylcarbamoyloxy-2-butynoate, ethyl 4-N-phenylcarbamoyloxy-2-butynoate, methyl 4-N-(p-chlorophenyl)-carbamoyloxy-2-butynoate, β-propoxyethyl 4-N,N-dimethylcarbamoyloxy-2-butynoate, ethyl 4-N,N-dicyclohexylcarbamoyloxy-2-butynoate, ethyl 4-N,N-diphenylcarbamoyloxy-2-butynoate, ethyl 4-piperidinocarbonyloxy-2-butynoate, ethyl 4-(4-methylpiperazino) carbonyloxy-2-butynoate, ethyl 4-morpholinocarbonyloxy-2-butynoate, ethyl 4-N,N-bis(β-chloroethyl)carbonyloxy-2-butynoate and ethyl 4-N-benzyl-N-methylcarbamoyloxy-2-butynoate. Particularly preferred are methyl 4-carbamoyloxy-2-butynoate, ethyl 4-carbamoyloxy-2-butynoate, isopropyl 4-carbamoyloxy-2-butynoate, isobutyl 4-carbamoyloxy-2-butynoate, β-propoxyethyl 4-carbamoyloxy-2-butynoate and β-propoxyethyl 4-N-methylcarbamoyloxy-2-butynoate. Most preferred are methyl 4-carbamoyloxy-2-butynoate and isopropyl 4-carbamoyloxy-2-butynoate.

Now, the present invention will be described in further detail with reference with Examples. However, it should be understood that the present invention is by no means restricted by these specific Examples.

Firstly, Examples for the preparation of 3-carbamoyloxyalkylpropiolic acid derivatives of the general formula VI of the present invention will be given. These Examples are identified by symbol "VI".

EXAMPLE VI-1

Preparation of methyl 4-carbamoyloxy-2-butynoate
$$H_2NCOOCH_2C≡CCOOCH_3$$

22.8 g (0.2 mole) of Methyl 4-hydroxy-2-butynoate was dissolved in 200 ml of dichloromethane, and 17.5 ml (0.2 mole) of chlorosulfonyl isocyanate was added thereto at a temperature of $-20°$ C. The mixture was stirred for 30 minutes at a temperature of from $-10°$ to $-20°$ C. To the reaction mixture, 20 ml of water was added, and hydrolysis treatment was carried out for 30 minutes at a temperature of about 0° C. Crystals formed in the reaction mixture were collected by filtration to obtain 18 g of primary crystals. The filtrate was subjected to phase separation. The dichloromethane phase obtained by the phase separation and the dichloromethane extraction solutions obtained by extraction treatment of the aqueous phase with dichloromethane, were put together, washed with water and then concentrated under reduced pressure, and the crystals thereby formed were collected to obtain 10 g of secondary crystals. The primary and secondary crystals were put together and recrystallized from ethylacetate, whereby 25.1 g (yield: 80%) of methyl 4-carbamoyloxy-2-butynoate in crystal form was obtained.

mp: 113°–114° C.

IR (KBr), cm$^{-1}$: 3410, 3350, 3300, 3220, 2250, 1750, 1700, 1620, 1440, 1320, 1295, 1090, 1050, 930, 750.

$^1$H NMR (90 MHz, DMSO-d$_6$), δ: 3.77 (s, 3H), 4.82 (s, 2H), 6.8 (broad s, 2H).

EXAMPLE VI-2 to VI-8

In the same manner as in Example VI-1, the compounds identified in Table VI-1 were obtained.

stirred for 30 minutes under cooling with ice. The reaction mixture was returned to room temperature and left to stand for one night. Then, the reaction mixture was concentrated under reduced pressure to distil off benzene, whereby 8.1 g (yield: 85%) of oily ethyl 4-(chlorocarbonyloxy)-2-butynoate was obtained as the residue.

IR (liquid film), cm$^{-1}$: 2250, 1785, 1720.

$^1$H NMR (90 MHz, CDCl$_3$), δ: 1.34 (t, 3H0, 4.28 (q,

TABLE VI-1

| Example Nos. | Compounds (VI) | Yields* | Melting point (°C.) | IR(KBr) cm$^{-1}$ | $^1$H—NMR(90 MHz) δ in ppm |
|---|---|---|---|---|---|
| VI-2 | H$_2$NCOOCH$_2$C≡CCOOC$_2$H$_5$ | 14.2 g 83% | 86–87 | 3480, 3350, 3290, 2250, 1755, 1720, 1600, 1410, 1325, 1250, 1050 | (DMSO-d$_6$); 1.24(t, 3H, J=7.5Hz), 4.21(q, 2H, J=7.5Hz), 4.82(s, 2H), 6.80 (br.s, 2H) |
| VI-3 | H$_2$NCOOCH$_2$C≡CCOOC$_3$H$_7$(n) | 13.9 g 75% | 134–136 | 3475, 3420, 3350, 3300, 2980, 2250, 740, 1710, 1690, 1610, 1405, 1390, 1320, 1300, 1270, 1250, 1240, 1090, 925, 780, 745 | (CDCl$_3$); 0.98(t, 3H, J=7Hz), 1.74(m, 2H), 4.19(t, 2H, J=7Hz), 4.85(s, 2H), 4.6~5.6(br.s, 2H) 1045, 950 |
| VI-4 | H$_2$NCOOCH$_2$C≡CCOOCH$_2$CH$_2$OC$_3$H$_7$(n) | 19.5 g 85% | Oily substance | 3500, 3380, 2980, 2900 2250, 1720, 1650, 1600 1430, 1390, 1330, 1260, 1150, 1130, 1090, 1055, 985, 780, 750 (Liquid film) | (CDCl$_3$); 0.92(t, 3H, J=7.5Hz), 1.6(m, 2H), 3.45(t, 2H, J=7Hz), 3.66(t, 2H, J=5Hz), 4.35(t, 2H, J=5Hz), 4.82(s, 2H), 4.9~5.4(br.s, 2H) |
| VI-5 | H$_2$HCOOCH$_2$C≡CCOOCH$_2$CH$_2$OCH$_2$CH=CH$_2$ | 16 g 70% | Oily substance | 3500, 3400, 2990, 2900, 2250, 1720, 1650, 1605, 1430, 1390, 1330, 1260, 1130, 1050, 990, 910, 750 (Liquid film) | (CDCl$_3$); 3.66(t, 2H, J=6Hz) 3.9(d, 2H, J=5Hz) 4.35(t, 2H, J=6Hz) 4.82(s, 2H) 5.2(broad s, 2H) 5.2(d, 2H, J=11Hz) 5.4~5.9(m, 1H) |
| VI-6 | H$_2$NCOOCH$_2$C≡CCOOCH$_2$CH$_2$OCH$_2$C$_5$H$_5$ | 20 g 72% | Oily substance | 3480, 3400, 3000, 2900, 2250, 1720, 1645, 1600, 1435, 1390, 1325, 1255, 1125, 1090, 1055, 780, 740, (Liquid film) | (CDCl$_3$); 3.66(t, 2H, J=5.5Hz) 4.35(t, 2H, J=5.5Hz) 4.52(s, 2H) 4.82(s, 2H) 5.2(broad s, 2H) 7.35(s, 5H) |
| VI-7 | H$_2$NCOOCH$_2$C≡CCOOCH$_2$CH$_2$OC$_6$H$_5$ | 17.2 g 60% | Oily substance | 3480, 3420, 2250, 1720, 1650, 1610, 1600, 1440, 1390, 1330, 1260, 1150, 1130, 1090, 1060, 780, 755 (Liquid film) | (CDCl$_3$); 3.65(t, 2H, J=6Hz) 4.35(t, 2H, J=6Hz) 4.8(s, 2H) 5.2(broad s, 2H) 6.9~7.5(m, 5H) |
| VI-8 | H$_2$NCOOCH$_2$C≡CCOOCH$_2$CH$_2$N(CH$_3$)(CH$_2$C$_6$H$_5$) | 17.7 g 61% | Oily substance | 3500, 3400, 2980, 2250, 1720, 1650, 1605, 1435, 3500, 1325, 1260, 1130, 1050, 780, 735 (Liquid film) | (CDCl$_3$); 2.15(s, 3H) 2.52(t, 3H, J=6Hz) 3.48(s, 2H) 4.12(t, 2H, J=6Hz) 4.8(s, 2H) 5.2(broad s, 2H) 7.34(s, 5H) |

*The yields of the compounds (VI) obtained by the reaction of 0.1 mole of the respective starting materials of the general formula VII.

EXAMPLE VI-9

Preparation of ethyl N-propylcarbamoyloxy-2-butynoate

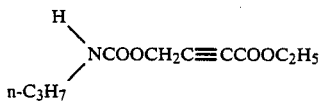

To 40 ml of a benzene solution of phosgene (containing 6.2 g (62.5 millimoles) of phosgene), 6.4 g (50 millimoles) of ethyl 4-hydroxy-2-butynoate was rapidly added under cooling with ice, and the mixture was 2H), 5.02 (s, 2H).

2.85 g (15 millimoles) of ethyl 4-(chlorocarbonyloxy)-2-butynoate was dissolved in 30 ml of benzene, and 12 ml of a benzene solution of propylamine (containing 2.22 ml (27 millimoles) of propylamine) was rapidly added thereto under cooling with ice. The mixture was stirred for 30 minutes under cooling with ice. The reaction mixture was poured into ice water and adjusted to pH 2 with dilute hydrochloric acid. To this mixture, 100 ml of ethyl acetate was added and stirred for extraction treatment. The ethyl acetate extraction solution was dried over sodium sulfate and concentrated under reduced pressure, whereby 3.08 g (yield: 96.2%) of oily ethyl N-propylcarbamoyloxy-2-butynoate was obtained.

IR (liquid film), cm$^{-1}$: 2250, 1785, 1720, 1250.

$^1$H NMR (90 MHz, CDCl$_3$), δ: 0.95 (t, 3H, J=7 Hz), 1.35 (t, 3H, J=7 Hz), 1.62 (m, 2H,), 3.20 (m, 2H,), 4.29 (q, 2H,), 4.86 (s, 2H,), 8.40 (broad, 1H).

EXAMPLE VI-10 to VI-21

In the same manner as in Example VI-9, the compounds identified in Table VI-2 were prepared.

TABLE IV-2

| Example Nos. | Compounds (VI) | Yields* | Melting point °C. | IR cm$^{-1}$ | $^1$H—NMR(90 MHz) δ in ppm |
|---|---|---|---|---|---|
| VI-10 | H\NCOOCH$_2$C≡CCOOC$_2$H$_5$ / CH$_3$ | 7.4 g 80% | Oily substance | 3400, 3000, 2950, 2240, 1720, 1710, 1530, 1365, 1245, 1130, 1070, 1010, 990, 770, 750, (Liquid film) | (CDCl$_3$); 1.37(t, 3H, J=7.5 Hz), 4.3(q, 2H, J=7.5Hz), 4.88(s, 2H), 4.8~5.2(m, 1H), 2.88(d, 3H, J=4.5Hz) |
| VI-11 | H\NCOOCH$_2$C≡CCOOCH$_2$CH$_2$Cl / CH$_3$ | 9.2 g 84% | 71-72 | 3350, 2950, 2250, 1710, 1700, 1575, 1455, 1310, 1290, 1280, 1260, 1250, 1160, 1100, 1010, 775, 750 (KBr) | (CDCl$_3$); 2.85(d, 3H, J=4.5 Hz), 3.75(t, 2H, J=7.5Hz), 4.47(t, 2H, J=7.5Hz), 4.87 (s, 2H), 4.7~5.3(m, 1H) |
| VI-12 | H\NCOOCH$_2$C≡CCOOCH$_2$CH=CH$_2$ / CH$_3$ | 7.4 g 75% | Oily substance | 3400, 2970, 2250, 1715, 1530, 1450, 1425, 1365, 1240, 1135, 1070, 995, 940, 775, 750 (Liquid film) | (CDCl$_3$); 2.83(d, 3H, J=6 Hz), 4.7(d, 2H, J=6Hz), 4.83(s, 2H), 4.6~5.1(m, 1H), 5.2~5.6(m, 2H), 5.7~6.3(m, 1H) |
| VI-13 | H\NCOOCH$_2$C≡CCOOCH$_2$C≡CH / CH$_3$ | 6.8 g 70% | Oily substance | 3440, 3370, 3300, 2960, 2250, 2140, 1720, 1530, 1440, 1420, 1370, 1240, 1130, 1070, 995, 775, 750 (Liquid film) | (CDCl$_3$); 2.55(t, 1H, J=3Hz) 2.83(d, 3H, J=5Hz) 4.79(d, 2H, J=3Hz) 4.7-5.05(m, 1H) 4.83(s, 2H) |
| VI-14 | H\NCOOCH$_2$C≡CCOOCH$_2$CH$_2$OC$_3$H$_7$(n) / CH$_3$ | 9.5 g 78% | Oily substance | 3380, 2980, 2890, 2250, 1720, 1530, 1450, 1365, 1245, 1130, 1070, 1015, 990, 770, 750 (Liquid film) | (CDCl$_3$); 0.93(t, 3H, J=7Hz), 1.63(m, 2H), 2.34(d, 3H, J=5Hz), 3.45(t, 2H, J=7Hz), 3.68(t, 2H, J=4.5Hz), 4.35(t, 2H, J=4.5Hz), 4.85 (s, 2H), 4.8~5.3(m, 1H) |
| VI-15 | H\NCOOCH$_2$C≡CCOOCH$_2$C$_6$H$_5$ / CH$_3$ | 8.7 g 70% | Oily substance | 3400, 2970, 2250, 1720, 1530, 1455, 1420, 1375, 1240, 1130, 1070, 995, 750, 700 (Liquid film) | (CDCl$_3$); 2.8(d, 3H, J=5Hz), 4.81(s, 2H), 4.7~5.1(m, 1H), 5.22(s, 2H), 7.4(s, 5H) |
| VI-16 | H\NCOOCH$_2$C≡CCOOC$_6$H$_5$ / CH$_3$ | 7.7 g 66% | Oily substance | 3450, 3380, 2970, 2250, 1730, 1530, 1495, 1230, 1190, 1130, 990, 750 (Liquid film) | (CDCl$_3$); 2.8(d, 3H, J=5Hz), 4.87(s, 2H), 4.7~5.2(m, 1H), 7.0-7.6(m, 5H) |
| VI-17 | H\NCOOCH$_2$C≡CCOOC$_2$H$_5$ / C$_2$H$_5$ | 7.8 g 78.5% | Oily substance | 3370, 3000, 2250, 1720, 1530, 1450, 1370, 1250, 1140, 1075, 1025, 770, 750 (Liquid film) | (CDCl$_3$); 1.18 (t, 3H, J=7.5Hz), 1.34(t, 3H, J=7Hz), 3.28(quintet, 2H, J=7~7.5Hz) 4.3(q, 2H, J=7Hz) 4.84(s, 2H), 4.8~5.1(m, 1H) |
| VI-18 | H\NCOOCH$_2$C≡CCOOCH$_3$ / CH$_3$ | 6.9 g 80.6% | Oily substance | 3400, 2970, 2250, 1720, 1535, 1435, 1250, 1130, 1070, 990, 940, 770, 750 (Liquid film) | (CDCl$_3$); 2.82(d, 3H, J=6Hz) 3.8(s, 3H) 4.82(s, 2H) 5.13(m, 1H) |
| VI-19 | H\NCOOCH$_2$C≡CCOOC$_2$H$_5$ / t-C$_4$H$_9$ | 6.8 g 60% | Oily substance | 3400, 2250, 1780, 1720, 1520, 1255 (Liquid film) | (CDCl$_3$); 1.32(t, 3H, J=7.5Hz) 1.37(s, 9H) 4.26(q, 2H, J=7.5Hz) 4.79(s, 2H) |

TABLE IV-2-continued

| Example Nos. | Compounds (VI) | Yields* | Melting point °C. | IR cm$^{-1}$ | $^1$H—NMR(90 MHz) δ in ppm |
|---|---|---|---|---|---|
| VI-20 | H\NCOOCH$_2$C≡CCOOC$_2$H$_5$ / C$_6$H$_{11}$ | 9.4 g 74.5% | 67–68 | 3350, 2970, 2250, 1715, 1695, 1530, 1450, 1320, 1265, 1250, 1235, 1145, 1085, 1050, 750 (KBr) | (CDCl$_3$); 1.34(t, 3H, J=7.5Hz) 1.2~2.2(m, 10H) 3.3~3.8(m, 1H) 4.28(q, 2H, J=7.5Hz) 4.7~5.1(m, 1H) 4.83(s, 2H) |
| VI-21 | H\NCOOCH$_2$C≡CCOOCH$_2$CH$_2$OC$_3$H$_7$(n) / C$_6$H$_{11}$ | 6.5 g 61.5% | Oily substance | 3360, 2950, 2870, 2250, 1720, 1530, 1450, 1365, 1250, 1230, 1130, 1075, 1045, 985, 970, 890, 770, 750 (Liquid film) | (CDCl$_3$); 0.92(t, 3H, J=8Hz), 1.65(m, 2H) 1.5~2.1(m, 10H) 3.3~3.8(m, 1H) 3.44(t, 2H, J=8Hz) 3.65(t, 2H, J=4.5Hz) 4.35(t, 2H, J=4.5Hz) 4.6~5.1(m, 1H), 4.8(s, 2H) |

*The yields of the compounds (VI) obtained by the reaction of 50 millimoles of the respective starting materials of the general formula VII.

EXAMPLE VI-22

Preparation of ethyl 4-N-phenylcarbamoyloxy-2-butynoate 6.4 g (0.05 mole) of ethyl 4-hydroxy-2-butynoate was dissolved in 100 ml of dichloromethane, and 6 ml (0.055 mole) of phenyl isocyanate and 0.5 ml of triethylamine were added thereto at a temperature of −20° C. The mixture was reacted for 1 hour under stirring. The reaction mixture was washed with 10 ml of 1N hydrochloric acid and water successively, then dried over magnesium sulfate and concentrated under reduced pressure. The residue was separated and purified by means of a liquid chromatography apparatus (System 500 A manufactured by Waters Co.) by using a silica gel column (Pre PAK-500 ®) and ethylacetate-hexane (1:3) as the developer solvent. Useful fractions were collected and concentrated under reduced pressure, whereby 10.6 g (yield: 85.8%) of oily ethyl 4-N-phenylcarbamoyloxy-2-butynoate was obtained.

IR (liquid film), cm$^{-1}$: 3350, 2250, 1720, 1540, 1255, 1210, 1050, 750.

$^1$H NMR (90 MHz, CDCl$_3$), δ (ppm): 1.33 (5, 3H, J=8.5 Hz), 4.3 (q, 2H, J=8.5 Hz), 4.92 (s, 2H), 6.9–7.2 (br. s), 7.3–7.6 (br. s, 5H).

EXAMPLE VI-23

Preparation of β-propoxyethyl 4-N,N-dietylcarbamoyloxy-2-butynoate

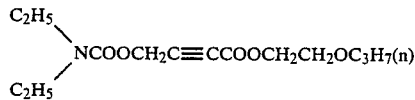

To 800 ml of a diethyl ether solution of phosgene (containing 248 g (2.5 moles) of phosgene), 112.1 g (2 moles) of propargyl alcohol was rapidly added under cooling with ice. The mixture was reacted for 2 hours under stirring and cooling with ice. The reaction mixture was returned to room temperature and left to stand one night. Then, the ether was distilled off. The residue was purified by vacuum distillation, whereby 194 g (yield: 81.8%) of colorless propargylchloroformate was obtained from the fraction distilled at a temperature of 47° C./40 mmHg to 44° C./34 mmHg.

Boiling point: 44° C./34 mmHg–47° C./40 mmHg.

$^1$H NMR (90 MHz, CDCl$_3$), δ: 2.68 (t, 1H, J=3 Hz), 4.88 (d, 2H, J=3 Hz).

To 200 ml of a benzene solution of diethylamine (containing 26 ml (249 millimoles) or diethylamine), 11.8 g (99.6 millimoles) of the propargyl chloroformate obtained as above, was added under cooling with ice. The mixture was reacted for 30 minutes under stirring and cooling with ice. The reaction mixture was poured into ice water and extracted with benzene. The benzene extraction solution was dried over sodium sulfate and then concentrated under reduced pressure. The residue was purified by vacuum distillation, whereby 14.7 g (yield: 95%) of colorless oily propargyl N,N-diethylcarbamate was obtained from the fraction distilled at a temperature of from 71° to 73° C./8 mmHg.

Boiling point: 71°–73° C./8 mmHg

IR (liquid film), cm$^{-1}$: 3320, 3270, 3000, 2140, 1700

$^1$H NMR (90 MHz, CDCl$_3$), δ: 1.16 (t, 6H, J=7.5 Hz), 2.48 (t, 1H, J=3 Hz), 3.33 (q, 4H, J=7.5 Hz), 4.73 (d, 2H, J=3 Hz).

To 60 ml of a tetrahydrofran solution containing 14.7 g (94.7 millimoles) of propargyl N,N-diethylcarbamate thus obtained, 57.4 ml (1.65 moles) of a hexane solution of butyl lithium (containing 94.7 millimoles of butyl lithium) was dropwise added at a temperature of from −65° to −75° C. (dryice, acetone cooling bath), and then 16.6 g (99.5 millimoles) of β-propoxyethylchloroformate was added at a temperature of from −60° to −70° C. The mixture was reacted for 30 minutes at a temperature of from −60° to −70° C. under stirring. Then, the cooling bath was removed, and when the liquid temperature reached room temperature, the reaction mixture was poured into ice water and extracted with ethylacetate. The ethylacetate extraction solution was dried and then concentrated under reduced pressure. The oily residue thereby obtained was purified by silica gel column chromatography (with use of 50 g silica gel). The desired fraction eluted by benzene was collected and concentrated under reduced pressure, whereby 12.65 g (yield: 46.8%) of colorless oily β- propoxyethyl 4-N,N-diethylcarbamoyloxy-2-butynoate was obtained.

IR (liquid film), cm$^{-1}$: 2250, 1750, 1710, 1430, 1255, 1165.

$^1$H NMR (90 MHz, CDCl$_3$), δ: 0.93 (t, 3H, J=7 Hz), 1.16 (t, 6H, J=7.5 Hz), 1.62 (m, 2H), 3.33 (q, 4H, J=7.5 Hz), 3.45 (t, 2H, J=7.5 Hz), 3.67 (t, 2H, J=7.5 Hz), 4.33 (t, 2H, J=7.5 Hz), 4.86 (s, 2H).

EXAMPLE VI-24 to VI-35

In the same manner as in Example VI-23, the compounds identified in Table VI-3 were prepared.

TABLE VI-3

| Example Nos. | Compounds (VI) | Yields* | Melting point °C. | IR cm$^{-1}$ | $^1$H—NMR(90MHz) δ in ppm |
|---|---|---|---|---|---|
| VI-24 | (CH$_3$)$_2$NCOOCH$_2$C≡CCOOCH$_2$CH$_2$OC$_3$H$_7$(n) | 9.8 g 38% | Oily substance | 2250, 1715, 1250, 1175 (Liquid film) | (CDCl$_3$); 0.93(t,3H,J=7.5Hz) 1.62(m,2H,) 2.96(s,6H,) 3.45(t,2H,J=7Hz) 3.66(t,2H,J=4.7Hz) 4.35(t,2H,J=4.7Hz) 4.84(s,2H) |
| VI-25 | (i-C$_3$H$_7$)$_2$NCOOCH$_2$C≡CCOOCH$_2$CH$_2$OC$_3$H$_7$(n) | 14.1 g 45% | Oily substance | 2250, 1705, 1440, 1250, 1050 (Liqiud film) | (CDCl$_3$); 0.92(t,3H,J=7.5Hz) 1.14(d,12H,J=7Hz) 1.61(m,2H), 3.44(t,2H), 3.67(t,2H,J=4.7Hz), 3.93(m,2H), 4.35(t,2H, J=4.7Hz), 4.85(s,2H) |
| VI-26 | (n-C$_4$H$_9$)$_2$NCOOCH$_2$C≡CCOOCH$_2$CH$_2$OC$_3$H$_7$(n) | 15.9 g 46.5% | Oily substance | 2250, 1710, 1425, 1250 (Liquid film) | (CDCl$_3$); 0.94(t,9H,J=7.5Hz) 1.1~1.8(m,10H), 3.24(t,4H, J=0.8Hz), 3.45(t,2H,J=6.8 Hz), 3.66(t,2H,J=4.7Hz), 4.35(t,2H,J=4.7Hz), 4.84(s,2H) |
| VI-27 | (ClCH$_2$CH$_2$)$_2$NCOOCH$_2$C≡CCOOC$_2$H$_5$ | 9.2 g 31% | Oily substance | (Liquid film): 1710,1465,1420, 1370,1320,1240, 1150,1000,880, 765,675 | (CDCl$_3$); 1.33(t,3H,J=7.5Hz) 3.5~4.0(m,8H) 4.25(q,2H,J=7.5Hz) 4.90(s,2H) |
| VI-28 | (C$_6$H$_{11}$)$_2$NCOOCH$_2$C≡CCOOC$_2$H$_5$ | 13.8 g 41% | Oily substance | (Liquid film): 2250,1785,1705, 1440,1240,1025 | (CDCl$_3$); 1.1~2.0(m,23H) 3.2~3.7(m,2H) 4.25(q,2H,J=7.5Hz) 4.83(s,2H) |
| VI-29 | (C$_6$H$_5$)$_2$NCOOCH$_2$C≡CCOOC$_2$H$_5$ | 17.8 g 55% | Oily substance | (Liquid film): 2250,1720,1600, 1500,1380,1260, 1210,1055,765, 755,700 | (CDCl$_3$); 1.30(t,3H,J=7.5Hz) 4.25(q,2H,J=7.5Hz) 4.90(s,2H) 7.34(s,10H) |
| VI-30 | pyrrolidino-NCOOCH$_2$C≡CCOOC$_2$H$_5$ | 10.4 g 46% | Oily substance | (Liquid film): 1710,1435,1180, 1030,860 | (CDCl$_3$); 1.30(t,3H,J=7.5Hz) 1.90(m,4H) 3.44(m,4H) 4.23(q,2H,J=7.5Hz) |
| VI-31 | piperidino-NCOOCH$_2$C≡CCOOC$_2$H$_5$ | 12.7 g 53% | Oily substance | (Liquid film): 1705,1440,1235, 1150,1030 | (CDCl$_3$); 1.30 (t,3H,J=7.5Hz) 1.62(m,6H) 3.53(m,4H) 4.23(q,2H,J=7.5Hz) 4.77(s,2H) |
| VI-32 | morpholino-NCOOCH$_2$C≡CCOOC$_2$H$_5$ | 14.0 g 58% | Oily substance | (Liquid film): 2250,1710,1435, 1240 | (CDCl$_3$); 1.34(t,3H,J=7.5Hz) 3.53(m,4H) 3.71(m,4H) 4.29(q,2H,J=7.5Hz) 4.88(s,2H) |
| VI-33 | CH$_3$—N(piperazino)NCOOCH$_2$C≡CCOOC$_2$H$_5$ | 16.0 g 63% | Oily substance | (Liquid film): 2250,1710,1435, 1365 | (CDCl$_3$); 1.33(t,3H,J=7.5Hz) 2.34(s,3H) 2.41(m,4H) 3.55(m,4H) 4.28(q,2H,J=7.5Hz) 4.86(s,2H) |

TABLE VI-3-continued

| Example Nos. | Compounds (VI) | Yields* | Melting point °C. | IR cm$^{-1}$ | $^1$H—NMR(90MHz) δ in ppm |
|---|---|---|---|---|---|
| VI-34 | HOCH$_2$CH$_2$\<br>　　　　＞NCOOCH$_2$C≡CCOOC$_2$H$_5$<br>HOCH$_2$CH$_2$/ | 9.1 g<br>35% | Oily substance | (Liquid film):<br>3420,1700,1470,<br>1420,1370,1320,<br>1260,1225,1145,<br>1050,860,770 | (CDCl$_3$);<br>1.29(t,3H,J=7.5Hz)<br>3.54(m,4H)<br>3.83(m,4H)<br>3.7∼4.3(broad,2H)<br>4.23(q,2H,J=7.5Hz)<br>4.86(s,2H) |
| VI-35 | HOCH$_2$CH$_2$\<br>　　　　＞NCOOCH$_2$C≡CCOOCH$_2$CH$_2$OC$_3$H$_7$(n)<br>HOCH$_2$CH$_2$/ | 8.9 g<br>28% | Oily substance | (Liquid film):<br>3420,1700,1475,<br>1420,1260,1220,<br>1125,1050,860,<br>770 | (CDCl$_3$);<br>0.93(t,3H,J=7.5Hz)<br>1.62(m,2H)<br>3.35∼4.0(m,12H)<br>4.08(broad s,2H)<br>4.32(t,2H,J=4.3Hz)<br>4.84(s,2H) |

*The yields of the compounds (VI) obtained by the reaction of 0.1 mole of the respective starting materials of the general formula IX.

EXAMPLE VI-36

Preparation of ethyl 4-(N-benzyl-N-methylcarbamoyloxy)-2-butynoate

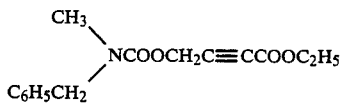

2.85 g (15 millimoles) of ethyl 4-(chlorocarbonyloxy)-2-butynoate obtained in the first step of Example VI-9 was dissolved in 20 ml of dichloromethane, and 9 ml of a dichloromethane solution containing 3.1 ml (24 millimoles) of N-methylbenzylamine was rapidly added under cooling with ice. The mixture was reacted for 1 hour under stirring and cooling with ice. The reaction mixture was poured into ice water, adjusted to pH 2 with dilute hydrochloride acid and subjected to extraction treatment. The dichloromethane extraction solution was dried over sodium sulfate and then concentrated under reduced pressure. The residue was purified by silica gel column chromatography (with use of 30 g of silica gel). The desired fraction eluted by hexane-benzene (1:0→3:1), was collected and concentrated under reduced pressure, whereby 1.18 g (yield: 28.5%) of colorless oily ethyl 4-(N-benzyl-N-methylcarbamoyloxy)-2-butynoate was obtained.

IR (liquid film), cm$^{-1}$: 2250, 1720, 1255, 1140. $^1$H NMR (90 MHz, CDCl$_3$), δ: 1.30 (t, 3H, J=7 Hz), 2.87 (s, 3H), 4.24 (q, 2H, J=7 Hz), 4.49 (s, 2H), 4.87 (s, 2H), 7.31 (s, 5H).

EXAMPLE VI-37

Preparation of ethyl 4-N-methylcarbamoyloxy-2-pentynoate

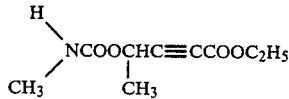

To 40 ml of a benzene solution containing 3.8 g (26.7 millimoles) of ethyl 4-hydroxy-2-pentynoate, 1.8 ml (30.5 millimoles) of methylisocyanate and 4.2 ml (30 millimoles) of polyethylamine were added, and the mixture was reacted for 1.5 hours at room temperature under stirring. The reaction mixture was washed with 50 ml of 1-N hydrochloric acid and water successively, dried over sodium sulfate and then concentrated under reduced pressure. The residue was purified by silica gel (Prep PAK 500/silica) column chromatography by means of a liquid chromatography apparatus (System 500 A manufactured by Waters Co.). The desired fraction eluted by hexane-ethylacetate (3:1) was collected and concentrated under reduced pressure, whereby 3.6 g (yield: 67%) of colorless oily ethyl 4-N-methylcarbamoyloxy-2-pentynoate was obtained.

IR (liquid film), cm$^{-1}$: 3360, 3000, 2850, 2250, 1710, 1530, 1470, 1450, 1420, 1370, 1240, 1130, 1095, 1050, 1020, 980, 940, 860, 775, 750.

$^1$H NMR (90 MHx, CDCl$_3$), δ: 1.3 (t, 3H, J=7.5 Hz), 1.53 (d, 3H, J=6 Hz), 1.82 (d, 3H, J=5.5 Hz), 4.25 (q, 2H, J=7.5 Hz), 4.6-5.1 (broad s, 1H), 5.54 (q, 1H, 6 Hz)

EXAMPLE VI-38

Preparation of ethyl 4-carbamoyloxy-4-methyl-2-pentynoate

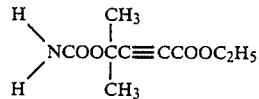

To 100 ml of a dichloromethane solution containing 4.9 g (31.4 millimoles) of ethyl 4-hydroxy-4-methyl-2-pentynoate, 3 ml (34.5 millimoles) of chlorosulfonyl isocyanate was added at a temperature of −10° C. The mixture was reacted for 30 minutes at −10° C. under stirring. The reaction mixture was returned to room temperature, and 20 ml of water was added thereto. The mixture was stirred for 15 minutes for hydrolysis treatment. The dichloromethane phase was separated by phase separation, washed with a 10% barium chloride solution and water successively, dried over sodium sulfate and then concentrated under reduced pressure, whereby 2.1 g (yield: 33%) of ethyl 4-carbamoyloxy-4-methyl-2-pentynoate in crystal form was obtained.

mp: 111°-113.5° C.

IR (KBr), cm$^{-1}$: 3580, 3360, 3300, 3220, 3020, 2240, 1710, 1605, 1380, 1370, 1265, 1230, 1145, 1050, 1035, 865, 785, 755.

EXAMPLE VI-39

Preparation of ethyl 5-N-methylcarbamoyloxy-2-pentynoate

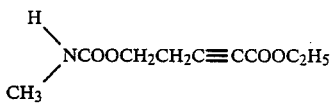

To 50 ml of a benzene solution containing 2.85 g (20 millimoles) of ethyl 5-hydroxy-2-pentynoate, 1.2 ml (20 millimoles) of methyl isocyanate and 2.8 ml (20 millimoles) of triethylamine were added, and the mixture was reacted for 1 hour at room temperature under stirring.

The reaction mixture was purified in the same manner as in Example VI-37, whereby 3.6 g (yield: 90.5%) of colorless oily ethyl 5-N-methylcarbamoyloxy-2-pentynoate was obtained.

IR (liquid film), cm$^{-1}$: 3400, 2970, 2240, 1710, 1530, 1470, 1370, 1250, 1140, 1075, 1010, 860, 775, 750.

$^1$H NMR (90 MHz, CDCl$_3$), δ in ppm: 1.33 (t, 3H, J=7 Hz), 2.63 (t, 2H, J=6 Hz), 2.83 (d, 3H, J=5 Hz), 4.25 (t, 2H, J=6 Hz), 4.27 (q, 2H, J=7 Hz), 4.75-5.1 (m, 1H).

EXAMPLE VI-40

Preparation of ethyl 4-carbamoyloxy-4-phenyl-2-butynoate

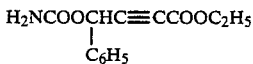

To 100 ml of a dichloromethane solution containing 8 g (39.2 millimoles) of ethyl 4-hydroxy-4-phenyl-2-butynoate, 3.5 ml (40.2 millimoles) of chlorosulfonyl isocyanate was added at a temperature of −20° C., and the mixture was reacted for 30 minutes at −10° C. under stirring. Then, hydrolysis and purification treatment were conducted in the same manner as in Example VI-38, whereby 9.5 g (yield: 98%) of ethyl 4-carbamoyloxy-4-phenyl-2-butynoate in crystal form was obtained.

mp: 82° C.

IR (KBr), cm$^{-1}$: 3460, 3350, 3290, 3010, 2950, 2250, 1730, 1705, 1605, 1500, 1465, 1365, 1280, 1260, 1195, 1090, 1015, 780, 760, 750, 700.

$^1$H NMR (90 MHz, CDCl$_3$), δ in ppm: 1.32 (t, 3H, J=7 Hz), 4.26 (q, 2H, J=7 Hz), 5.05 (broad s, 2H), 6.51 (s, 1H), 7.46 (broad s, 5H).

Now, Examples for the preparation of the novel 3-amino-3-carbamoyloxyalkyl acrylic acid derivatives of the general formula II of the present invention will be given.

EXAMPLE II-1

Preparation of ethyl 3-amino-4-methylcarbamoyloxycrotonate

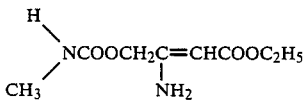

1.85 g (10 millimoles) of ethyl 4-N-methylcarbamoyloxy-2-butynoate and 3.84 g (50 millimoles) of ammonium acetate were dissolved in 20 ml of ethanol and reacted at 60° C. for 4 hours under stirring. The reaction mixture was concentrated under reduced pressure. To the residue, 50 ml of ethylacetate and 10 ml of a 20% sodium chloride aqueous solution were added for extraction reatment. The ethylacetate extraction solution was dried over magnesium sulfate and concentrated under reduced pressure. The residue was purified by silica gel (Prep PAK 500/silica) column chromatography by means of a liquid chromatography apparatus (System 500 A manufactured by Waters Co.). The desired fraction eluted by hexane-ethylacetate (5:4) was collected and concentrated under reduced pressure, whereby 0.88 g (yield: 44%) of ethyl 3-amino-4-N-methylcarbamoyloxycrotonate in crystal form was obtained.

mp: 60°-61° C.

UV: λ$_{max}^{MeOH}$ 274 nm (ε 14000).

IR(KBr), cm$^{-1}$: 3450, 3350, 3000, 2950, 1720, 1660, 1620, 1590, 1540, 1445, 1370, 1280, 1190, 1170, 1055, 1040, 955, 790.

$^1$H NMR (90 MHz, CDCl$_3$), δ in ppm: 127 (t, 3H, J=75 Hz), 283 (d, 3H, J=6 Hz), 4.6 (s, 2H), 4.66 (s, 1H), 4.75-5.1 (m, 1H), 6.1-6.8 (broad, 2H).

EXAMPLE II-2 to II-27

In the same manner as in Example II-1, the compounds identified in Table II-1 were prepared.

TABLE II-1

R$^5$\\NCOOCH$_2$C=CHCOOR$^3$ / R$^6$ , NH$_2$

| Example Nos. | R$^5$ | R$^6$ | R$^3$ | Yields* | Melting point °C. | UV λ$_{max}^{MeOH}$ nm |
|---|---|---|---|---|---|---|
| II-2 | H | H | CH$_3$ | 0.94 g 54% | 90~92 | 274 |
| II-3 | H | H | C$_2$H$_5$ | 0.98 g 52% | 42~44 | 274 |
| II-4 | H | H | n-C$_3$H$_7$ | 0.83 g 41% | Oily substance | 274 |
| II-5 | H | H | CH$_2$CH$_2$OC$_3$H$_7$(n) | 1.04 g | Oily sub- | 274 |

TABLE II-1-continued $$\begin{array}{c}R^5\\ \diagdown\\ \diagup N COOCH_2C=CHCOOR^3\\ R^6 \quad\quad | \\ \quad\quad\quad NH_2\end{array}$$

| | | 45% | stance |

*The yields of the compounds (II) obtained by the reaction of 10 millimoles of the respective starting materials of the general formula VI.

| Example Nos. | IR cm$^{-1}$ | $^1$H-NMR(90MHz) δ in ppm |
|---|---|---|
| II-2 | (KBr): 3500, 3370, 3220, 1730, 1650, 1620, 1570, 1440, 1400, 1335, 1280, 1170, 1070, 950, 920, 800, 785 | (CDCl$_3$): 3.64(s, 3H) 4.58(s, 2H) 4.63(s, 1H) 5.9(broad s, 2H) 6.4~7.2(broad, 2H) |
| II-3 | (KBr): 3520, 3370, 3250, 1730, 1660, 1625, 1565, 1390, 1335, 1290, 1170, 1110, 1040, 950, 780 | (DMSO-d$_6$): 1.17(t, 3H, J=7.5Hz) 4.05(q, 2H, J=7.5Hz) 4.5(s, 2H) 4.52(s, 1H) 6.76(s, 2H) 7.2(broad s, 2H) |
| II-4 | (Liquid film): 3480, 3360, 2990, 1725, 1660, 1625, 1570, 1440, 1385, 1335, 1330, 1285, 1170, 1070, 790 | (DMSO-d$_6$): 0.9(t, 3H, J=7Hz) 1.6(m, 2H) 4.0(t, 2H, J=7Hz) 4.52(s, 2H) 4.55(s, 1H) 6.73(broad s, 2H) 6.9~7.5(broad, 2H) |
| II-5 | (Liquid film): 3460, 3350, 2970, 2880, 1720, 1660, 1625, 1570, 1440, 1385, 1330, 1280, 1165, 1040, 785 | (CDCl$_3$):0.9(t, 3H, J=7.5Hz) 1.6(m, 2H) 3.44(t, 2H, J=7.5Hz) 3.65(t, 2H, J=6Hz) 4.24(t, 2H, J=6Hz) 4.6(s, 2H), 5.0~5.6 (s, 2H) 6.1~6.9(broad s, 2H) |

| Example Nos. | Compounds (II) | | | Yields | Melting point °C. | UV $\lambda_{max}^{MeOH}$ nm |
|---|---|---|---|---|---|---|
| | R$^5$ | R$^6$ | R$^3$ | | | |
| II-6 | H | H | CH$_2$CH$_2$OCH$_2$CH=CH$_2$ | 0.85 g 35% | Oily substance | 274 |
| II-7 | H | H | CH$_2$CH$_2$OCH$_2$C$_6$H$_5$ | 1.18 g 40% | Oily substance | 274 |
| II-8 | H | H | CH$_2$CH$_2$N(CH$_3$)(CH$_2$C$_6$H$_5$) | 1.24 g 40.5% | Oily substance | 274 |
| II-9 | H | CH$_3$ | CH$_3$ | 0.90 g 48% | 146–147 | 273 |

| Example Nos. | IR cm$^{-1}$ | $^1$H-NMR(90MHz) δ in ppm |
|---|---|---|
| II-6 | 3450, 3350, 2970, 2880, 1720, 1650, 1630, 1570, 1440, 1380, 1330, 1280, 1160, 1040, 1000, 940, 870, 785, (Liquid film) | (CDCl$_3$):3.65(t, 2H, J=3.5Hz), 4.0(d, 2H, J=9Hz), 4.25(t, 2H, J=3.5Hz), 4.6(s, 2H), 4.7(s, 1H), 5.1~5.5(m, 4H), 5.6~6.2(m, 1H), 6.3~6.9(broad, 2H) |
| II-7 | 3450, 3350, 2980, 2890, 1725, 1665, 1620, 1560, 1440, 1375, 1280, 1260, 1060, 1040, 1000, 985, 940, 695 (Liquid film) | (CDCl$_3$):3.64(t, 2H, J=4Hz), 4.20(t, 2H, J=4Hz), 4.52(s, 2H), 4.6(s, 2H), 4.7(s, 1H), 5.0~5.4(broad, 2H), 6.2~6.9(broad, 2H), 7.4(s, 5H) |
| II-8 | 3460, 3350, 2970, 1720, 1660, 1625, 1570, 1440, 1385, 1330, 1280, 1160, 1040, 780, 740, 695 (Liquid film) | (CDCl$_3$):2.20(s, 3H), 2.62(t, 2H, J=6Hz), 3.5(s, 2H), 4.17(t, 2H, J=6Hz), 4.6(s, 2H), 4.7(s, 1H), 5.18(broad s, 2H), 6.2~6.9(broad, 2H), 7.27(s, 5H) |

TABLE II-1-continued $$R^5\diagdown N\text{COOCH}_2\underset{\underset{NH_2}{|}}{C}{=}\text{CHCOOR}^3$$
$$R^6\diagup$$

| Example Nos. | IR cm$^{-1}$ | $^1$H-NMR(90MHz) δ in ppm |
|---|---|---|
| II-9 | (KBr): 3450, 3350, 1710, 1680, 1620, 1590, 1535, 1425, 1380, 1290, 1255, 1175, 1140, 980, 790 | (DMSO-d$_6$): 2.6(d, 3H, J=4.5Hz) 3.54(s, 3H) 4.52(s, 3H) 6.7~7.7 (broad, 3H) |

| Example Nos. | Compounds (II) | | | Yields | Melting point °C. | UV $\lambda_{max}^{MeOH}$ nm |
|---|---|---|---|---|---|---|
| | R$^5$ | R$^6$ | R$^3$ | | | |
| II-10 | H | CH$_3$ | CH$_2$CH$_2$Cl | 1.37 g 58% | Oily substance | 274 |
| II-11 | H | CH$_3$ | CH$_2$CH=CH$_2$ | 1.0 g 46.5% | Oily substance | 274 |
| II-12 | H | CH$_3$ | CH$_2$C≡CH | 0.81 g 38% | Oily substance | 273 |
| II-13 | H | CH$_3$ | CH$_2$CH$_2$OC$_3$H$_7$(n) | 1.16 g 44.5% | Oily substance | 274 |

| Example Nos. | IR cm$^{-1}$ | $^1$H-NMR(90MHz) δ in ppm |
|---|---|---|
| II-10 | 3450, 3350, 2950, 1720, 1665, 1620, 1560, 1540, 1450, 1420, 1380, 1280, 1255, 1160, 1140, 1100, 1040, 1020, 900, 780 (Liquid film) | (CDCl$_3$): 2.85(d, 3H, J=6Hz) 3.7(t, 2H, J=6Hz) 4.35(t, 2H, J=6Hz) 4.63(s, 2H), 4.7(s, 1H), 4.8~5.3(m, 1H) 6.1~6.9(s, 2H) |
| II-11 | 3450, 3350, 2950, 1720, 1655, 1600, 1565, 1440, 1420, 1370, 1260, 1165, 1140, 1040, 990, 935, 790 (Liquid film) | (CDCl$_3$): 2.85(d, 3H, J=6Hz), 4.6(d, 2H, J=4.5Hz), 4.62(s, 2H), 4.69(s, 1H), 5.0~5.5(m, 2H), 5.7~6.2(m, 1H), 5.7~6.7(broad, 2H), 6.2~6.9(broad, 1H) |
| II-12 | 3440, 3350, 2950, 2130, 1720, 1670, 1620, 1560, 1540, 1440, 1420, 1370, 1280, 1260, 1160, 1100, 1040, 1000, 940, 900, 785 (Liquid film) | (CDCl$_3$): 2.44(t, 1H, J=3Hz) 2.82(d, 3H, J=5.5Hz) 4.6(s, 1H) 4.68(d, 2H, J=3Hz) 4.69(s, 2H), 4.9~5.13(m, 1H), 6.3~6.8(broad, 2H) |
| II-13 | 3450, 3350, 2970, 2880, 1720, 1665, 1625, 1570, 1440, 1370, 1330, 1280, 1260, 1165, 1130, 1045, 790 (Liquid film) | (CDCl$_3$): 0.92(t, 3H, J=7.5Hz), 1.6(m, 2H), 2.82(d, 3H, J=6Hz), 3.44(t, 2H, J=7.5Hz), 3.63(t, 2H, J=4.5Hz), 4.23(t, 2H, J=4.5Hz), 4.6(s, 2H), 4.9~5.4(m, 1H), 6.1~6.9(broad, 2H) |

| Example Nos. | Compounds (II) | | | Yields | Melting point °C. | UV $\lambda_{max}^{MeOH}$ nm |
|---|---|---|---|---|---|---|
| | R$^5$ | R$^6$ | R$^3$ | | | |
| II-14 | H | CH$_3$ | CH$_2$C$_6$H$_5$ | 0.87 g 33% | Oily substance | 274 |
| II-15 | H | CH$_3$ | C$_6$H$_5$ | 0.90 g 36% | Oily substance | 274 |
| II-16 | H | C$_2$H$_5$ | C$_2$H$_5$ | 0.91 g 47.5% | Oily substance | 274 |
| II-17 | H | t-C$_4$H$_9$ | C$_2$H$_5$ | 0.92 g 37.5% | Oily substance | 274 |

| Example Nos. | IR cm$^{-1}$ | $^1$H-NMR(90MHz) δ in ppm |
|---|---|---|
| II-14 | 3450, 3350, 2950, 1725, 1665, 1620, 1560, 1450, 1370, 1280, 1260, 1060, | (DMSO-d$_6$): 2.63(d, 3H, J=5Hz) 4.55(s, 2H) 4.6(s, 1H) |

TABLE II-1-continued $$\begin{array}{c} R^5 \\ \diagdown \\ R^6 \diagup \end{array} NCOOCH_2C=CHCOOR^3 \\ \phantom{XXXXXXXXXX} | \\ \phantom{XXXXXXXXXX} NH_2$$

| Example Nos. | IR cm$^{-1}$ | $^1$H-NMR(90MHz) δ in ppm |
|---|---|---|
| | 1040, 1000, 905, 785, 740, 695 (Liquid film) | 5.08(s, 2H) 7.1~7.6(broad, 3H) 7.4(s, 5H) |
| II-15 | 3450, 3350, 2950, 1720, 1670, 1625, 1570, 1370, 1260, 1200, 1135, 1040, 1020, 960, 790 770 (Liquid film) | (DMSO-d$_6$): 2.65(d, 3H, J=5Hz) 4.54(s, 2H) 4.64(s, 1H) 6.7~7.8(m, 8H) |
| II-16 | 3460, 3360, 3000, 1720, 1665, 1630, 1575, 1535, 1450, 1370, 1290, 1250, 1070, 1095, 1030, 790 (Liquid film) | (CDCl$_3$): 1.16(t, 3H, J=7.5HZ) 1.27(t, 3H, J=7Hz) 3.27(m, 2H) 4.15(q, 2H, J=7Hz) 4.6(s, 2H), 4.66(s, 1H) 5.08(m, 1H) 5.9~6.9(s, 2H) |
| II-17 | 3450, 3350, 2980, 1720, 1660, 1620, 1570, 1525, 1455, 1365, 1285, 1265, 1210, 1165, 1085, 1040, 910, 780 (Liquid film) | (CDCl$_3$): 1.25(t, 3H, J=8Hz) 1.33(s, 9H) 4.13(q, 2H, J=8Hz) 4.53(s, 2H) 4.65(s, 1H) 4.76~5.03(broad, 1H) 6.16~6.76(broad, 2H) |

| Example Nos. | Compounds (II) | | | Yields | Melting point °C. | UV $\lambda_{max}^{MeOH}$ nm |
|---|---|---|---|---|---|---|
| | R$^5$ | R$^6$ | R$^3$ | | | |
| II-18 | H | cyclohexyl-H | C$_2$H$_5$ | 0.68 g 25% | Oily substance | 274 |
| II-19 | H | cyclohexyl-H | CH$_2$CH$_2$OC$_3$H$_7$(n) | 0.94 g 28.5% | Oily substance | 274 |
| II-20 | H | phenyl | C$_2$H$_5$ | 0.91 g 34.5% | Oily substance | 274 |
| II-21 | H | n-C$_3$H$_7$ | C$_2$H$_5$ | 0.89 g 38.5% | Oily substance | 274 |

| Example Nos. | IR cm$^{-1}$ | $^1$H-NMR(90MHz) δ in ppm |
|---|---|---|
| II-18 | 3460, 3360, 2950, 1715, 1665, 1625, 1570, 1530, 1450, 1365, 1280, 1250, 1230, 1170, 1040, 790 (Liquid film) | (CDCl$_3$): 1.25(t, 3H, J=7Hz), 1.5~2.2(m, 10H), 3.3~3.7(m, 1H), 4.15(q, 2H, J=7Hz), 4.58(s, 2H), 4.66(s, 1H), 4.6~5.1(m, 1H), 6.2~6.9(broad, 2H) |
| II-19 | 3470, 3360, 2960, 2880, 1715, 1670, 1630, 1575, 1530, 1455, 1385, 1370, 1280, 1260, 1235, 1170, 1130, 1060, 1050, 890, 790 (Liquid film) | (CDCl$_3$):0.92(t, 3H, J=7Hz), 1.65(m, 2H), 1.5~2.2(m, 10H), 3.3~3.7(m, 1H), 3.45(t, 2H, J=7Hz), 3.64(t, 2H, J=6Hz), 4.24(t, 2H, J=6Hz), 4.59(s, 2H), 4.7(s, 1H), 4.6~5.1(m, 1H), 6.1~6.9(br, 2H) |
| II-20 | 3460, 3350, 3000, 1710, 1640, 1600, 1570, 1540, 1445, 1370, 1280, 1260, 1210, 1050, 900, 845, 750 (Liquid film) | (CDCl$_3$): 1.25(t, 3H, J=8Hz) 4.13(q, 2H, J=8Hz) 4.6(s, 2H), 4.65(s, 1H) 6.1~7.3(broad, 1H) 7.41(s, 5H) |
| II-21 | 3460, 3360, 3000, 1720, 1665, 1630, | (CDCl$_3$):0.93(t, 3H, J=7.5Hz), 1.26(t, 3H, J=7.5Hz), |

TABLE II-1-continued $$\begin{array}{c} R^5 \\ \diagdown \\ \diagup N\text{COOCH}_2\text{C}=\text{CHCOOR}^3 \\ R^6 \quad | \\ \quad \text{NH}_2 \end{array}$$

| | | |
|---|---|---|
| 1575, 1535, 1460, 1450, 1370, 1290, 1275, 1240, 1170, 1150, 1100, 1040, 790 (Liquid film) | 1.56(m, 2H), 3.18(q, 2H, J=7.5Hz), 4.15(q, 2H, J=7.5Hz), 4.6(s, 2H), 4.66(s, 1H), 4.9~5.3(m, 1H), 6.1~6.9(broad, 2H) | |

| Example Nos. | Compounds (II) R⁵ | R⁶ | R³ | Yields | Melting point °C. | UV $\lambda_{max}^{MeOH}$ nm |
|---|---|---|---|---|---|---|
| II-22 | H | 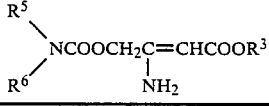 4-Cl-C₆H₄ | C₂H₅ | 11.9 g 39.7% | Oily substance | 274 |
| II-23 | H | 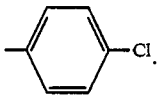 4-Cl-C₆H₄ | CH₃ | 12.7 g 44.6% | Oily substance | 274 |
| II-24 | H | H | CH₂CH₂OCH₃ | 10.5 g 48.1% | Oily substance | 274 |
| II-25 | H | 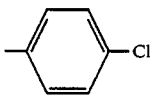 cyclohexyl | CH₂CH₂OCH₃ | 11.9 g 39.6% | Oily substance | 274 |
| II-26 | H | 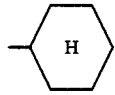 4-Cl-C₆H₄ | CH₂CH₂OC₃H₇ | 11.2 g 34.8% | Oily substance | 274 |
| II-27 | H | 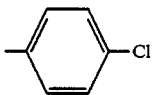 2,3-diCl-C₆H₃ | CH₂CH₂OC₃H₇ | 14.7 g 37.5% | Oily substance | 274 |

| Example Nos. | IR cm⁻¹ | ¹H-NMR(90MHz) δ in ppm |
|---|---|---|
| II-22 | (Liquid film): 3450, 3350, 1720, 1665, 1625, 1290, 1175, 830, 770, 740 | (CDCl₃): 1.25(t, 3H, J=7.5Hz), 4.15(q, 2H, J=7.5Hz), 4.6(s, 1H), 4.67(s, 2H), 5.9–7.0(broad, 2H), 7.45(d, 2H, J=8.5Hz), 7.63(d, 2H, J=8.5Hz) |
| II-23 | (Liquid film): 3460, 3350, 1710, 1670, 1630, 1290, 1170, 1145, 830, 790, 740 | (DMSO-d₆): 3.54(s, 3H), 4.52(s, 3H), 6.5–7.7(broad, 3H), 7.48(d, 2H, J=8.0Hz) 7.65(d, 2H, J=8.0Hz) |
| II-24 | (Liquid film): 3460, 3350, 2970, 1720, 1660, 1625, 1330, 1280, 1160, 1035, 785 | (CDCl₃): 3.42(s, 3H), 3.65(t, 2H, J=4Hz), 4.23(t, 2H, J=4Hz), 4.6(s, 2H), 4.69(s, 1H), 5.27(broad, s, 2H), 6.1–6.9(broad, 2H) |
| II-25 | (Liquid film): 3470, 3360, 2950, 1710, 1665, 1625, 1280, 1165, 1040, 700 | (CDCl₃): 0.9–2.2(m, 10H), 3.4(s, 3H), 3.3–3.7(m, 1H), 3.64(t, 2H, J=4Hz), 4.23(t, 2H, J=4Hz), 4.58(s, 2H), 4.65(s, 1H), 4.6–5.1(m, 1H), 6.0–6.9(broad, 2H) |
| II-26 | (Liquid film): 3440, 3340, 2970, 1720, 1665, 1625, 1570, 1255, 1165, 1130, 830, 770, 740 | (CDCl₃): 0.94(t, 3H, J=7Hz), 1.3–1.9(m, 2H), 3.45(t, 2H, J=7Hz), 3.67(t, 2H, J=5Hz), 4.35(t, 2H, J=5Hz), 4.59(s, 2H), 4.68(s, 1H), 4.9–5.45(broad, 1H), 6.0–7.0(broad, 2H), 7.45(d, 2H, J=8Hz), 7.65(d, 2H, J=8Hz) |
| II-27 | (Liquid film): 3440, 3340, 2970, 1720, 1660, 1620, 1570, 1530, 1280, 1260, 1165, 1130, | (CDCl₃): 0.92(t, 3H, J=8.5Hz), 1.3–1.9(m, 2H), 3.44(t, 3H, J=8.5Hz), 3.63(t, 2H, J=4.5Hz), 4.22(t, 2H, |

TABLE II-1-continued $$\begin{array}{c}R^5\\ \diagdown\\ \phantom{R^6\diagup}NCOOCH_2C=CHCOOR^3\\ \diagup\phantom{NCOOCH_2}|\\ R^6\phantom{\diagup NCOOCH_2}NH_2\end{array}$$

| | |
|---|---|
| 810, 750 | J=4.5Hz), 4.62(s, 2H), 4.71(s, 1H), 4.9-5.5(broad, 1H), 6.1-6.9(broad, 2H), 7.4(d, 1H, J=8Hz), 7.52(d, 1H, J=8Hz), 7.7(s, 1H) |

EXAMPLE II-28

Preparation of β-propoxyethyl 3-amino-4-N,N-diethylcarbamoyloxycrotonate

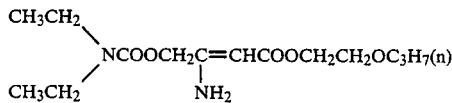

12.5 g (43.8 millimoles) of β-propoxyethyl 4-N,N-diethylcarbamoyloxy-2-butynoate was dissolved in 180 ml of isopropyl alcohol, and 11 ml of 28% aqueous ammonia was added. The mixture was reacted at 60° C. for 1 hour under stirring. The reaction mixture was concentrated under reduced pressure. The residue was extracted with ethylacetate. The ethylacetate extraction solution was subjected to water-removal treatment and then concentrated under reduced pressure. The residue was purified by silica gel (Prep PAK 500/silica) column chromatography by means of a chromatography apparatus (SYSTEM 500 A manufactured by Waters Co.). The desired fraction eluted by hexane-ethylacetate (2:1) was collected and concentrated under reduced pressure, whereby 8.6 g (yield: 65%) of colorless oily β-propoxyethyl 3-amino-4-N,N-diethylcarbamoyloxycrotonate was obtained.

UV: $\lambda_{max}.^{MeOH}$ 275nm (ε 13500).

IR (Liquid film), cm$^{-1}$: 3450, 3350, 2980, 1695, 1625, 1575, 1480, 1430, 1380, 1365, 1275, 1160, 1120, 1095, 1070, 1005, 790, 765.

$^1$H NMR (90 MHz, CDCl$_3$), δ in ppm: 0.92 (t, 3H, J=8 Hz), 1.15 (t, 6H, J=7.5 Hz), 1.62 (m, 2H), 3.32 (q, 4H, J=7.5 Hz), 3.45 (t, 2H, J=8 Hz), 3.65 (t, 2H, J=4.5 Hz), 4.25 (t, 2H, J=4.5 Hz), 4.62 (s, 2H), 4.71 (s, 1H), 6.0–7.0 (broad, s, 2H).

EXAMPLE II-29 to II-40

In the same manner as in Example II-28, the compounds identified in Table II-2 were prepared.

TABLE II-2

$$R-COOCH_2C=CHCOOR^3\\ \phantom{R-COOCH_2C=CH}|\\ \phantom{R-COOCH_2C=CH}NH_2$$

| Example Nos. | Compounds (II) R | R$^3$ | Yields* | Melting point °C. | UV $_{max.}^{MeOH}$ nm | IR cm$^{-1}$ | $^1$H—NMR(90MHz) δ in ppm |
|---|---|---|---|---|---|---|---|
| II-29 | CH$_3$\N—/CH$_3$ | CH$_2$CH$_2$OC$_3$H$_7$(n) | 1.92 g 70% | Oily substance | 274 | 3460,3350,2970, 2900,1710,1675, 1630,1575,1400, 1360,1280,1190, 1165,1120,1060, 790,770 (Liquid film) | (CDCl$_3$); 0.93(t,3H,J=8Hz) 1.63(m,2H), 2.98(s,6H) 3.46(t,2H,J=8Hz), 3.65 (t,2H,J=5Hz), 4.25(t,2H, J=5Hz), 4.62(s,2H), 4.74 (s,1H), 6.2~6.9(broad,2H) |
| II-30 | i-C$_3$H$_7$\N—/i-C$_3$H$_7$ | CH$_2$CH$_2$OC$_3$H$_7$(n) | 1.49 g 45% | Oily substance | 274 | 3450,3350,2990, 2900,1680,1630, 1570,1465,1440, 1370,1310,1290, 1220,1160,1135, 1060,995,790, 770 (Liquid film) | (CDCl$_3$); 0.92(t,3H,J=8Hz), 1.25(d, 12H,J=8Hz), 14~1.85(m,2 H),3.45(t,2H,J=8Hz), 3.65 (t,2H,J=6Hz), 3.98(q,2H, J=8Hz), 4.25(t,2H,J=6Hz) 4.62(s,2H), 4.73(s,1H) 6.2~6.8(broad,2H) |
| II-31 | n-C$_4$H$_9$\N—/n-C$_4$H$_9$ | CH$_2$CH$_2$OC$_3$H$_7$(n) | 1.47 g 41% | Oily substance | 275 | 3450,2970,2890, 1700,1630,1570, 1470,1420,1370, 1290,1220,1160, 1110,790,770 (Liquid film) | (CDCl$_3$); 0.93(t,9H,J=7Hz),1.05~ 1.8(m,10H), 3.25(t,4H,J= 7Hz), 3.44(t,2H,J=7Hz) 3.65(t,2H,J=4.5Hz), 4.25 (t,2H,J=4.5Hz), 4.61(s,2H), 4.71(s,1H), 6.2~6.9(broad,2H) |
| II-32 | ClCH$_2$CH$_2$\N—/ClCH$_2$CH$_2$ | C$_2$H$_5$ | 1.46 g 46.5% | Oily substance | 275 | 3460,3350,3000, 2970,1710,1670, 1630,1575,1470, 1410,1365,1280, 1260,1205,1170, 1145,1075,1005, 990,880,790, 770 (Liquid film) | (CDCl$_3$); 1.38(t,3H,J=7.5Hz) 3.77(t,2H,J=3.5Hz) 3.93(t,2H,J=3.5Hz) 4.16(q,2H,J=7.5Hz) 4.68(s,2H), 4.73(s,1H) 6.1~6.8(broad,2H) |

TABLE II-2-continued $$R-COOCH_2C=CHCOOR^3$$
$$|$$
$$NH_2$$

| Example Nos. | Compounds (II) R | R³ | Yields* | Melting point °C. | UV $MeOH_{max.}$ nm | IR cm$^{-1}$ | $^1$H—NMR(90MHz) δ in ppm |
|---|---|---|---|---|---|---|---|
| II-33 | $C_6H_{11}$\N—\$C_6H_{11}$ | $C_2H_5$ | 1.16 g 33% | 87.5 | 274 | 3420,3330,2950, 2860,1690,1660, 1630,1565,1445, 1350,1290,1265, 1235,1170,1160, 1090,1030,895, 790,765 (KBr) | (CDCl₃); 1.26(t,3H,J=7.5Hz) 1.4~2.1(m,20H) 3.2~3.8(m,2H) 4.15(q,2H,J=7.5Hz) 4.6(s,2H), 4.68(s,1H) 6.1~7.0(broad,2H) |
| II-34 | $C_6H_5$\N—\$C_6H_5$ | $C_2H_5$ | 1.38 g 40.5% | 115.8-117 | 237, 273 | 3450,3350,3000, 1670,1630,1585, 1490,1410,1350, 1310,1290,1175, 1065,1050,970, 795,750,700 (KBr) | (CDCl₃); 1.25(t,3H,J=7Hz) 4.13(q,2H,J=7Hz) 4.6(s,1H) 4.68(s,2H) 5.8~6.7(broad,2H) 7.1~7.6(m,5H) |
| II-35 | (pyrrolidinyl)N— | $C_2H_5$ | 1.24 g 51% | Oily substance | 274 | 3460,3360,3000, 2900,1700,1670, 1625,1575,1440, 1420,1370,1350, 1340,1290,1165, 1130,1100,1050, 790,770 (Liquid film) | (CDCl₃); 1.26(t,3H,J=7Hz) 1.89(m,4H),3.42(m,4H) 4.15(q,2H,J=7Hz) 4.62(s,2H) 4.67(s,1H) 6.0~7.0(broad,2H) |
| II-36 | (piperidinyl)N— | $C_2H_5$ | 1.35 g 52.5% | Oily substance | 274 | 3450,3350,2950, 2870,1700,1670, 1625,1570,1440, 1365,1285,1260, 1235,1160,1150, 1090,1025,790 (Liquid film) | (CDCl₃); 1.28(t,3H,J=7Hz) 1.62(broad,s,6H) 3.48(broad,s,4H) 4.17(q,2H,J=7 Hz) 4.64(s,2H),4.69(s,1H) 6.0~7.0(broad,2H) |
| II-37 | (morpholinyl) O\_/N— | $C_2H_5$ | 1.12 g 43.5% | Oil substance | 274 | 3450,3350,2980, 2860,1700,1670, 1625,1570,1460, 1430,1365,1280, 1240,1165,1115, 1090,1070,1040, 970,850,790, 760 (Liquid film) | (CDCl₃); 1.28(t,3H,J=7.5Hz) 3.53(t,4H,J=8Hz) 3.71(t,4H,J=4.5Hz) 4.18(q,2H,J=7.5 Hz) 4.65(s,2H),4.7(s,1H) 6.0~7.0(broad,2H) |
| II-38 | $CH_3$—N\_/N— | $C_2H_5$ | 1.52 g 56% | Oil substance | 273 | 3460,3350,2960, 2820,1710,1675, 1630,1575,1465, 1440,1370,1295, 1260,1240,1170, 1150,1110,1075, 1050,1010,790, 765 (Liquid film) | (CDCl₃); 1.26(t,3H,J=7.5Hz) 2.33(s,3H) 2.42(t,4H,J=4Hz) 3.55(t,4H,J=4Hz) 4.15(q,2H,J=7.5Hz) 4.62(s,2H),4.67(s,1H) 6.0~7.0(broad s,2H) |
| II-39 | $CH_3$\N—\$C_6H_5CH_2$ | $C_2H_5$ | 105 g 36% | Oil substance | 273 | 3460,3350,3000, 2950,1710,1670, 1630,1570,1480, 1455,1405,1370, 1290,1230,1170, 1145,1040,790, 770,700 (Liquid film) | (CDCl₃); 127(t,3H,J=7.5Hz) 415(q,2H,J=7.5Hz) 4.5(s,2H) 4.67(s,3H) 6.0~7.0(broad,2H) 7.1~7.6(broad,5H) |
| II-40 | $HOCH_2CH_2$\N—\$HOCH_2CH_2$ | $C_2H_5$ | 0.83 g 30% | Oil substance | 274 | 3450,3350,2960, 1690,1630,1570, 1470,1420,1370, 1290,1220,1170, 1140,1070,1045, 860,790,770 (Liquid film) | (CDCl₃); 1.24(t,3H,J=7Hz) 3.51(t,4H,J=4.5Hz) 3.8(t,4H,J=4.5Hz) 4.1(q,2H,J=7Hz) 4.26(s,2H), 4.63(s,3H) 6.5~6.9(broad,2H) |

*The yields of the compounds (II) obtained by the reaction of 10 millimoles of the respective starting materials of the general formula VI.

EXAMPLE II-41

Preparation of ethyl 3-amino-4-N-methylcarbamoyloxycrotonate 1.85 g (10 millimoles) of ethyl 4-N-methylcarbamoyloxy-2-butynoate and 3.95 g (50 millimoles) of ammonium bicarbonate were dissolved in 20 ml of methyl cellosolve and reacted at 60° C. for 4 hours. The subsequent treatments were conducted in the same manner as in Example II-1, whereby 0.8 g (yield: 40%) of ethyl 3-amino-4-N-methylcarbamoyloxycrotonate in crystal form was obtained.

mp: 60°–61° C.

The analytical results by IR(KBr), UV and $^1$H-NMR agreed very well to the results obtained with respect to the compound of Example II-1.

EXAMPLE II-42

Preparation of ethyl 3-amino-4-N-methylcarbamoyloxycrotonate 1.85 g (10 millimoles) of ethyl 4-N-methylcarbamoyloxy-2-butynoate and 1.73 g (12.5 millimoles) of ammonium benzoate were dissolved in 20 ml of dimethylformamide and reacted at 60° C. for 1 hour under stirring. The subsequent treatments were conducted in the same manner as in Example II-1, whereby 1.1 g (yield: 55%) of ethyl 3-amino-4-N-methylcarbamoyloxycrotonate was obtained.

mp: 60°–61° C.

The analytical results by IR(KBr), UV and $^1$H-NMR agreed very well to the results obtained with respect to the compound of Example II-1.

EXAMPLE II-43

Preparation of ethyl 3-amino-4-N-methylcarbamoyloxy-2-pentenoate

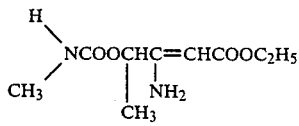

3.6 g (18 millimoles) of ethyl 4-N-methylcarbamoyloxy-2-pentynoate and 1.5 g (19.5 millimoles) of ammonium acetate were dissolved in 20 ml of dimethylformamide and reacted at 60° C. for 2 hours under stirring.

The reaction mixture was concentrated under reduced pressure. The residue was dissolved in a mixed solution of 50 ml of ethylacetate and water and stirred for mixing. The ethylacetate extraction solution was washed with water, then dried over magnesium sulfate and concentrated under reduced pressure. The residue was purified by silica gel (Prep PAK 500/silica) column chromatography by means of a liquid chromatography apparatus (System 500 A manufactured by Waters Co.). The desired fraction eluted by hexane-ethylacetate (2:1) was collected and concentrated under reduced pressure, whereby 2 g (9.3 millimoles, yield: 52%) of oily ethyl 3-amino-4-N-methylcarbamoyloxy-2-pentenoate was obtained.

UV: $\lambda_{max}.^{MeOH}$ 274 nm.

IR (liquid film), cm$^{-1}$: 3440, 3350, 3000, 1710, 1660, 1620, 1580, 1445, 1360, 1310, 1260, 1165, 1140, 1090, 1030, 955, 790.

$^1$H-NMR (90 MHz, CDCl$_3$), δ in ppm: 1.25 (t, 3H, J=7 Hz), 1.43 (d, 3H, J=7.5 Hz), 2.8 (d, 3H, J=6 Hz), 4.13 (q, 2H, J=7 Hz), 4.66 (s, 1H), 4.75–5.16 (broad, 1H), 5.23 (q, 1H, J=7 Hz), 5.9–6.9 (broad, 2H).

EXAMPLE II-44

Preparation of ethyl 3-amino-4-carbamoyloxy-4-methyl-2-pentenoate

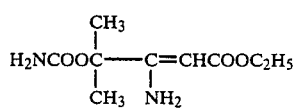

The reaction and purification treatment were conducted in the same manner as in Example II-43 except that 2.1 g (10.5 millimoles) of ethyl 4-carbamoyloxy-4-methyl-2-pentynoate was used as the starting material, whereby 0.47 g (2.1 millimoles, yield: 20%) of ethyl 3-amino-4-carbamoyloxy-4-methyl-2-pentenoate in crystal form was obtained.

mp: 109°–111° C.

UV: $\lambda_{max}.^{MeOH}$ 227 nm.

IR(KBr), cm$^{-1}$: 3460, 3350, 3290, 3220, 3000, 1735, 1650, 1630, 1610, 1555, 1360, 1295, 1200, 1160, 1140, 1100, 1025, 1000, 790.

$^1$H-NMR (90 MHz, CDCl$_3$), δ in ppm: 1.26 (t, 3H, J=7.5 Hz), 1.62 (s, 6H), 4.15 (q, 2H, J=7.5 Hz), 4.7 (s, 1H), 5.06 (s, 2H), 6.3–6.9 (broad, 2H).

EXAMPLE II-45

Preparation of ethyl 3-amino-5-N-methylcarbamoyloxy-2-pentenoate

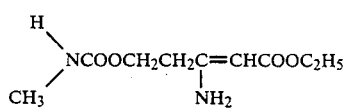

The reaction and purification treatment were conducted in the same manner as in Example II-43 except that 3.6 g (18 millimoles) of ethyl 5-N-methylcarbamoyloxy-2-pentynoate was used as the starting material, whereby 0.48 g (2.2 millimoles, yield: 12.2%) of oily ethyl 3-amino-5-N-methylcarbamoyloxy-2-pentenoate was obtained.

UV: $\lambda_{max}.^{MeOH}$ 276 nm.

IR (liquid film), cm$^{-1}$: 3475, 3360, 3000, 1730, 1660, 1615, 1430, 1385, 1350, 1270, 1170, 1100, 1040, 790.

$^1$H-NMR (90 MHz, CDCl$_3$), δ in ppm: 1.32 (t, 3H, J=8 Hz), 3.83 (t, 2H, J=7.5 Hz), 4.06 (t, 2H, J=7.5 Hz), 4.25 (q, 2H, J=8 Hz), 4.83 (s, 1H), 5.2–5.4 (broad s, 2H), 6.3–7.0 (broad, 2H).

EXAMPLE II-46

Preparation of ethyl 3-amino-4-carbamoyloxy-4-phenylcrotonate

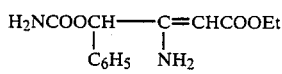

The reaction and purification treatments were conducted in the same manner as in Example II-37 except that 4.95 g (20 millimoles) of ethyl 4-carbamoyloxy-4-phenyl-2-butynoate was used as the starting material, whereby 1.9 g (yield: 26.1%) of oily ethyl 3-amino-4-carbamoyloxy-4-phenylcroronate was obtained.

UV: $\lambda_{max.}^{MeOH}$ 274 nm.

IR (liquid film), cm$^{-1}$: 3450, 3350, 3200, 3000, 1740, 1660, 1630, 1570, 1500, 1450, 1370, 1320, 1305, 1280, 1260, 1200, 1170, 1060, 1025, 965, 755, 695.

$^1$H-NMR (90 MHz, CDCl$_3$), δ in ppm: 1.34 (t, 3H, J=7 Hz), 4.28 (q, 2H, J=7 Hz), 4.83 (s, 1H), 5.1–5.3 broad s, 2H), 6.1–6.8 (broad, 2H), 7.5 (broad s, 5H).

Now, the process for the preparation of 2-carbamoyloxyalkyl-1,4-dihydropyridine derivatives according to the present invention will be specifically described.

EXAMPLE I-1

Preparation of 2-carbamoyloxymethyl-6-methyl-4-(o-nitrophenyl)-3,5-diethoxycarbonyl-1,4-dihydropyridine 9.4 g (50 millimoles) of ethyl 4-carbamoyloxy-3-aminocrotonate and 13.2 g (50 millimoles) of ethyl 2-(o-nitrobenzylidene)acetoacetate were dissolved in 200 ml of ethanol and reacted at a temperature of from 60° to 70° C. for 16 hours under stirring. The reaction mixture was concentrated under reduced pressure. The residue was crystallized from ethylacetate-hexane, whereby 12.6 g (yield: 58%) of 2-carbamoyloxymethyl-6-methyl-4-(o-nitrophenyl)-3,5-diethoxycarbonyl-1,4-dihydropyridine in crystal form was obtained.

mp: 128°–132° C.

UV: $\lambda_{max.}^{MeOH}$ 235, 350 nm.

IR (KBr): 3540, 3400, 3000, 1710, 1690, 1535, 1495, 1340, 1205, 1120, 1100, 1095, 780, 755, 715 cm$^{-1}$.

NMR (90 MHz, CDCl$_3$): δ 1.18 (t, J=7 Hz, 6H), 2.35 (s, 3H), 4.15 (m, 4H), 5.38 (broad s, 4H), 5.96 (s, 1H), 7.1–8.0 (m, 5H).

EXAMPLE I-2 to I-6

In the same manner as in Example I-1, the compounds identified in Table I-3 were prepared.

TABLE I-3

| Example No. | Compounds (I) | Yield | Melting Point °C. | UV $\lambda_{max}^{MeOH}$, nm |
|---|---|---|---|---|
| I-2 | (3-nitrophenyl dihydropyridine with CH$_3$OOC, COOCH$_3$, CH$_3$, CH$_2$O—CONH$_2$ substituents) | 12.2 g 60% | 110–114 | 235 355 |
| I-3 | (3-nitrophenyl dihydropyridine with C$_2$H$_5$OOC, COOC$_2$H$_5$, CH$_3$, CH$_2$O—CONH$_2$ substituents) | 13.7 g 63% | 144–148 | 235 355 |
| I-4 | (3-nitrophenyl dihydropyridine with (CH$_3$)$_2$CHOOC, COOC$_2$H$_5$, CH$_3$, CH$_2$O—CONH$_2$ substituents) | 9.4 g 42% | 130–132 | 235 355 |

TABLE I-3-continued

| | | | | |
|---|---|---|---|---|
| I-5 | [structure: dihydropyridine with 3-NO$_2$-phenyl, Cl-CH$_2$CH$_2$OOC, COOCH$_3$, CH$_3$, CH$_2$O-CONH$_2$, NH] | 11.8 g 52% | 166-168 | 236 355 |
| I-6 | [structure: dihydropyridine with 3-NO$_2$-phenyl, Cl-CH$_2$CH$_2$OOC, COOCH$_2$CH$_2$OC$_3$H$_7$, CH$_3$, CH$_2$O-CONH$_2$, NH] | 12.6 g 48% | — | 236 355 |

| Example No. | IR(KBr): cm$^{-1}$ | $^1$H NMR (90 MHz, CDCl$_3$): δ in ppm |
|---|---|---|
| I-2 | 3540, 3360, 2980, 1715, 1690, 1495, 1355, 1340, 1210, 1105, 1090, 830, 805, 790, 755, 710 | 2.38(s,3H),3.72(s,6H),5.2(s,1H), 5.35(s,2H),5.4(s,2H),7.3-8.25(m,5H) |
| I-3 | 3540, 3380, 3000, 1710, 1690, 1490, 1355, 1335, 1210, 1105, 1090, 790, 760, 720 | 1.23(t,J=7Hz,6H),2.4(s,3H),4.18(q,J= 7Hz,4H),5.2(s,1H),5.3(s,2H),5.4(s,2H), 7.2-8.2(m,5H) |
| I-4 | 3450, 3350, 2980, 1705, 1685, 1530, 1485, 1350, 1205, 1100, 1080, 780, 715 | 1.14(t,J=8Hz,3H),1.27(d,J=6Hz, 6H),1.42(s,3H),4.15(q,J=8Hz,2H), 5.0(sep,J=6Hz,1H),5.14(s,1H),5.3 (s,2H),6.1(m,2H),7.5-8.4(m,5H) |
| I-5 | 3420, 2960, 1740, 1710, 1685, 1645, 1600, 1530, 1475, 1350, 1320, 1205, 1070, 900, 830, 755 | 2.44(s,3H),3.7(s,3H),3.7(t,J= 6Hz,2H),4.36(t,J=6Hz,2H),5.1-5.8 (br.s,2H),5.2(s,1H),5.33(s,2H), 7.45-8.3(m,5H) |
| I-6 | 3500, 3400, 3000, 1710, 1690, 1640, 1600, 1530, 1490, 1350, 1210, 1100, 900, 780, 760, 720 | 0.8,(t,J=7Hz,3H),1.46(q,J=7Hz,2H) 2.35(s,3H),3.3(t,J=7Hz,2H),3.5(t,J= 6Hz,2H),3.75(t,J=5Hz,2H),4.1(t,J= 6Hz,2H),4.24(t,J=5Hz,2H),4.92(d,J= 12Hz,1H),5.05(s,1H),5.06(d,J=12Hz, 1H),6.6(broad-s,2H),7.3-8.1(m,4H), 9.0(s,1H) |

EXAMPLE I-7

Preparation of 2-N-methylcarbamoyloxymethyl-6-methyl-4-(o-nitrophenyl)-3,5-diethoxycarbonyl-1,4-dihydropyridine 10.1 g (50 millimoles) of ethyl 4-N-methylcarbamoyloxy-3-aminocrotonate and 13.2 g (50 millimoles) of ethyl 2-(o-nitrobenzylidene)acetoacetate were dissolved in 200 ml of ethanol and reacted at a temperature of from 60° to 70° C. for 16 hours under stirring. The reaction mixture was concentrated under reduced pressure. The residue was crystallized from diisopropylether-hexane, whereby 12.4 g (yield: 55.5%) of 2-N-methylcarbamoyloxymethyl-6-methyl-4-(o-nitrophenyl)-3,5-diethoxycarbonyl-1,4-dihydropyridine in crystal form was obtained.

mp: 165°-169° C.

UV: $\lambda_{max}.^{MeOH}$ 235, 350 nm.

IR (KBr): 3380, 3000, 1690, 1680, 1535, 1495, 1355, 1280, 1205, 1100, 785, 760, 715 cm$^{-1}$.

NMR (90 MHz, CDCl$_3$): δ 1.2 (t, J=7 Hz, 6H), 2.38 (s, 3H), 2.91 (d, J=6 Hz, 3H), 4.18 (m, 4H), 5.15 (m, 1H), 5.38 (s, 2H), 5.98 (s, 1H), 7.2-8.0 (m, 5H).

EXAMPLE I-8 to I-17

In the same manner as in Example I-7, the compounds identified in Table I-4 were prepared.

TABLE I-4

| Example No. | Compounds (I) | Yield | Melting Point °C. | UV $\lambda_{max}^{MeOH}$, nm |
|---|---|---|---|---|

TABLE I-4-continued
| No. | Structure | Yield | m.p. (°C) | λmax |
|---|---|---|---|---|
| I-8 | 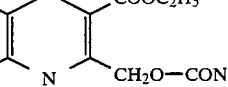 | 14.3 g 63.9% | 192–193 | 235 355 |
| I-9 | 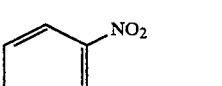 | 12.4 g 59% | 151–153 | 235 355 |
| I-10 | 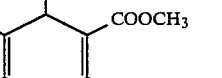 | 10.6 g 46% | 194–196 | 235 355 |
| I-11 | 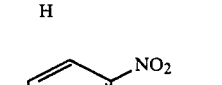 | 14.5 g 62% | 194–195 | 236 355 |
| I-12 | 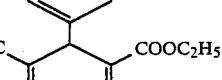 | 11.1 g 48% | 153–154.5 | 235 355 |
| Example No. | IR(KBr): cm$^{-1}$ | $^1$H NMR(90 MHz)*: δ in ppm |
|---|---|---|
| I-8 | 3400, 3300, 3000, 1690, 1685, 1480, 1355, 1280, 1205, 1105, 790, 760, 720, | (b); 1.18(t,J=7Hz,6H),2.38(s,3H), 2.67(d,J=5Hz,3H),4.12(q,J=7Hz,4H) 5.13(s,3H),7.22(m,1H),7.5–8.3(m,4H), 9.13(s,1H) |
| I-9 | 3350, 2950, 1700, 1685, 1530, 1480, 1350, 1210, 1095, 780, 705 | (a); 2.38(s,3H),2.88(d,J=5Hz,3H), 3.72(s,6H),5.2(s,2H),5.4(s,2H), 7.35–8.3(m,5H) |
| I-10 | 3380, 3290, 2980, 1680, 1525, 1480, 1350, 1275, 1250, 1205, 1100, 780, 715 | (b); 1.0–1.3(m,9H),2.38(s,3H),2.67 (m,3H),4.1(q,J=7Hz,2H),4.93(sep,J= 6Hz,1H),5.1(s,3H),7.2(m,1H), 7.4–8.2(m,4H),9.1(s,1H) |
| I-11 | 3400, 3300, 2960, 1690, 1640, 1610, 1530, 1480, 1350, 1280, 1260, 1210, 1110, 905, 830, 780, 760, 715 | (a); 2.47(s,3H),2.85(d,J=5Hz,3H), 3.73(s,3H),3.75(t,J=6Hz,2H), 4.4(t,J=6Hz,2H),5.22(s,1H),5.34 (s,2H),6.7(q,J=5Hz,1H),7.45–8.5 (m,5H) |
| I-12 | 3350, 2980, 1685, 1530, 1480, 1350, 1275, 1250, 1205, 1095, 780, 715 | (b); 0.9–1.3(m,12H),2.34(s,3H),3.07 (q,J=7Hz,2H),4.07(q,J=8Hz,2H), 4.9(m,1H),5.06(s,3H),7.28(t,J=7Hz, |

TABLE I-4-continued

1H),7.5-8.2(m,4H),9.05(br.s,1H)

| Example No. | Compounds (I) | Yield | Melting Point °C. | UV $\lambda_{max}^{MeOH}$, nm |
|---|---|---|---|---|
| I-13 | [structure: 1,4-dihydropyridine with 3-NO2-phenyl, CH(CH3)2-OOC, COOC2H5, CH3, CH2O-CONH-C3H7] | 9.5 g 40% | 150.5–152 | 235 355 |
| I-14 | [structure: 1,4-dihydropyridine with 3-NO2-phenyl, CH(CH3)2-OOC, COOC2H5, CH3, CH2O-CONH-cyclohexyl] | 10.8 g 42% | 157–159.5 | 235 355 |
| I-15 | [structure: 1,4-dihydropyridine with 3-NO2-phenyl, CH(CH3)2-OOC, COOC2H5, CH3, CH2O-CONH-phenyl] | 10.7 g 41% | 134–136 | 238 356 |
| I-16 | [structure: 1,4-dihydropyridine with 3-NO2-phenyl, CH(CH3)2-OOC, COOC2H5, CH3, CH2O-CONH-C6H4-Cl(4)] | 11.2 g 40% | 113–116.5 | 235 355 |
| I-17 | [structure: 1,4-dihydropyridine with 3-NO2-phenyl, Cl-CH2CH2OOC, COOCH3, CH3, CH2O-CONH-C6H4-Cl(4)] | 12.7 g 45% | — | 243 355 |

| Example No. | IR(KBr): cm$^{-1}$ | $^1$H NMR(90 MHz)*: δ in ppm |
|---|---|---|
| I-13 | 3350, 2980, 1685, 1530, 1480, 1355, 1270, 1240, 1207, 1100, 780, 715 | (b); 0.88(t,J=8Hz,3H),1.0–1.3(m,9H), 1.48(m,2H),2.38(s,3H),3.04(q,J=7Hz, 2H),4.12(q,J=8Hz,2H),4.14(m,1H), 5.1(s,3H),7.36(t,J=7Hz,1H),7.6– 8.3(m,4H),9.1(s,1H) |
| I-14 | 3350, 2940, 1680, 1530, 1480, 1350, 1275, 1207, 1095, 780, 710 | (b); 1.0–1.4(m,9H),1.4–2.0(m,10H), 2.37(s,3H),3.35(br.s,2H),4.1(q,J= 8Hz,2H),4.93(m,1H),5.1(s,3H) |
| I-15 | 3350, 2980, 1685, 1530, 1480, 1350, 1205, 1100, 740, 710, 690 | (b); 1.0–1.4(m,9H),2.4(s,3H),4.12(q,J= 8Hz,2H),4.93(m,1H),5.1(s,1H), 5.25(s,2H), 7.0–8.3(m,9H), 9.27(s,1H), 9.86(s,1H) |
| I-16 | 3380, 2980, 1695, 1530, | (b); 0.95–1.35(m,9H),2.37(s,3H), |

TABLE I-4-continued

|  | | |
|---|---|---|
| | 1350, 1220, 1100, 825, 740, 705 | 4.08(q,J=8Hz,2H),4.93(m,1H),5.1(s,1H), 5.36(s,2H),7.3–8.3(m,8H),9.27 (s,1H),10.0(s,1H) |
| I-17 | 3400, 3000, 1750, 1690, 1670, 1600, 1530, 1480, 1350, 1220, 1100, 900, 805, 750, 700 | — |

*; (a): CDCl$_3$, (b): DMSO-d$_6$

EXAMPLE I-18

Preparation of 2-carbamoyloxymethyl-6-methyl-4-(m-nitrophenyl)-3-ethoxycarbonyl-5-(β-ethoxyethoxy)carbonyl-1,4-dihydropyridine 9.4 g (50 millimoles) of ethyl 4-carbamoyloxy-3-aminocrotonate and 15.4 g (50 millimoles) of β-ethoxyethyl 2-(m-nitrobenzylidene)acetoacetate were dissolved in 200 ml of isopropyl alcohol and reacted at a temperature of from 60° to 70° C. for 18 hours. The reaction mixture was concentrated under reduced pressure. The residue was crystallized from diisopropylether-hexane, whereby 12.9 g (yield: 54%) of 2-carbamoyloxymethyl-6-methyl-4-(m-nitrophenyl)-3-ethoxycarbonyl-5-(β-ethoxyethoxy)carbonyl-1,4-dihydropyridine in crystal form was obtained.

mp: 135°–138° C.

UV: $\lambda_{max}^{MeOH}$ 236, 355 nm.

IR (KBr): 3520, 3360, 1990, 1705, 1690, 1645, 1610, 1525, 1485, 1350, 1205, 1120, 1105, 1055, 905, 830, 780, 755, 720 cm$^{-1}$.

NMR (90 MHz, DMSO-d$_6$): δ1.07 (t, J=8 Hz, 3H), 1.15 (t, J=3 Hz, 3H), 2.37 (s, 3H), 3.45 (q, J=8 Hz, 2H), 3.62 (t, J=4 Hz, 2H), 4.08 (q, J=8 Hz, 2H), 4.12 (t, J=4 Hz, 2H), 4.97 (d, J=12 Hz, 1H), 5.1 (s, 1H), 5.13 (d, J=12 Hz, 1H), 6.7 (br. s, 2H), 7.6–8.2 (m, 4H), 9.11 (s, 1H).

EXAMPLE I-19 to I-32:

In the same manner as in Example I-18, the compounds identified in Table I-5 were prepared.

TABLE I-5

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-19 | (3-NO$_2$-C$_6$H$_4$)-dihydropyridine with C$_3$H$_7$OCH$_2$CH$_2$OOC, COOC$_2$H$_5$, CH$_3$, CH$_2$O—CONH$_2$ | 12.5 g 51% | 147–149 | 236 355 | 3520, 3350, 2950, 1700, 1645, 1610, 1520, 1480, 1350, 1330, 1270, 1200, 1120, 1100, 1080, 905, 830, 780, 755, 720 | 0.85(t,J=8Hz,3H),1.18(t,J=8Hz,3H),1.5(m,2H),2.39(s,3H),3.36(t,J=8Hz,2H),3.57(t,J=5Hz,2H),4.12(q,J=8Hz,2H),4.15(t,J=5Hz,2H),5.0(d,J=13Hz,1H),5.12(s,1H),5.15(d,J=13Hz,1H),6.68(br.s,2H),7.5–8.3(m,4H),9.05(s,1H) |
| I-20 | (3-NO$_2$-C$_6$H$_4$)-dihydropyridine with i-C$_3$H$_7$OCH$_2$CH$_2$OOC, COOC$_2$H$_5$, CH$_3$, CH$_2$O—CONH$_2$ | 11.6 g 45% | 139–142 | 235 355 | 3520, 3360, 2980, 1702, 1685, 1645, 1610, 1525, 1485, 1350, 1330, 1270, 1200, 1120, 1080, 900, 825, 780, 755, 720 | 1.06(d,J=6Hz,6H),1.16(t,J=7Hz,3H),2.37(s,3H),3.55(m,1H),3.62(t,J=6Hz,2H),4.09(q,J=7Hz,2H),4.12(t,J=6Hz,2H),4.97(d,J=12Hz,1H),5.1(s,1H),5.13(d,J=12Hz,1H),6.65(br.s,2H),7.5–8.3(m,4H),9.10(s,1H) |
| I-21 | (3-NO$_2$-C$_6$H$_4$)-dihydropyridine with C$_2$H$_5$OOC, COOCH$_2$CH$_2$OCH$_3$, CH$_3$, CH$_2$O—CONH$_2$ | 9.7 g 42% | 121–125 | 236 355 | 3480, 3380, 2990, 1690, 1645, 1610, 1530, 1490, 1350, 1275, 1210, 1110, 1095, 1080, 905, 830, 780, 755, 720 | 1.16(t,J=8Hz,3H),2.38(s,3H),3.28(s,3H),3.53(t,J=5Hz,2H),4.08(q,J=8Hz,2H),4.18(t,J=5Hz,2H),5.0(d,J=13Hz,1H),5.11(s,1H),5.13(d,J=Hz,1H),6.7(br.s,2H),7.5–8.3(m,4H),9.07(s,1H) |

TABLE I-5-continued
| Example No. | Compounds (I) | Yield | Melting Point °C. | UV $\lambda^{MeOH}_{max}$ nm | IR(KBr): cm$^{-1}$ | $^1$H NMR (90 MHz, DMSO-d$_6$): δ in ppm |
|---|---|---|---|---|---|---|
| I-22 | 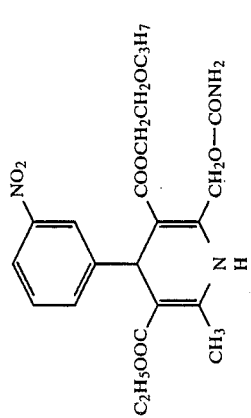 | 10.8 g 44% | 136–138.5 | 236 355 | 3500, 3380, 2980, 1710, 1680, 1640, 1600, 1525, 1490, 1350, 1275, 1210, 1095, 905, 830, 780, 760, 715 | 0.83(t,J=7Hz,3H),1.15(t,J=7Hz,3H), 1.5(m,2H),2.37(s,3H),3.35(t,J=7Hz, 2H),3.56(t,J=3Hz,2H),4.08(q,J=7Hz,2H), 4.16(t,J=3Hz,2H),5.0(d,J=13Hz,1H), 5.1(s,1H),5.15(d,J=13Hz,1H),6.72(s,2H), 7.5–8.3(m,4H),9.07(s,1H) |
| I-23 | 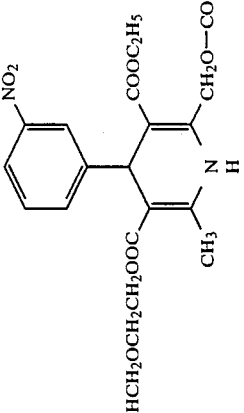 | 11.7 g 48% | 135–139 | 236 355 | 3520, 3360, 2990, 1705, 1685, 1640, 1610, 1520, 1485, 1350, 1330, 1270, 1200, 1120, 1100, 1080, 1000, 920, 900, 825, 780, 755, 720 | 1.16(t,J=8Hz,3H),2.38(s,3H),3.58 (t,J=5Hz,2H),3.98(d,J=9Hz,2H),4.1 (q,J=8Hz,2H),4.15(t,J=5Hz,2H),5.08 (d,J=10Hz,1H),5.1(s,1H),5.1–5.4 (m, 2H ),5.15(d,J=10Hz,1H),5.6–6.2 (m,1H),6.71(s,2H),7.5–8.3(m,4H), 9.11(s,1H) |
| I-24 | 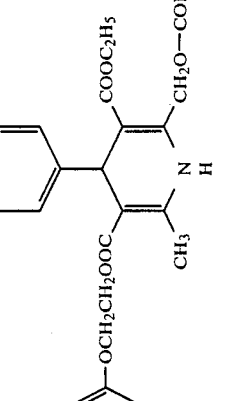 | 9.7 g 37% | 89–93 | 235 355 | 3480, 3420, 3360, 2950, 1710, 1690, 1615, 1600, 1530, 1490, 1350, 1335, 1250, 1200, 1125, 1080, 930, 915, 780, 755, 720, 690 | 1.16(t,J=9Hz,3H),2.4(s,3H),3.64 (t,J=7Hz,2H),4.1(q,J=9Hz,2H),4.25 (t,J=7Hz,2H),5.0(d,J=13Hz,1H),5.11 (s,1H),5.16(d,J=13Hz,1H),6.73(br.s, 2H),6.9–7.5(m,5H),7.4–8.3(m,4H), 9.16(s,1H) |

TABLE I-5-continued

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-25 | 3-NO$_2$-C$_6$H$_4$ dihydropyridine with C$_6$H$_5$CH$_2$OCH$_2$CH$_2$OOC— and —COOC$_2$H$_5$, CH$_3$ and —CH$_2$O—CONH$_2$ substituents | 12.4 g 46% | 58.5-62 | 236 355 | 3500, 3360, 2950, 1720, 1700, 1685, 1640, 1610, 1530, 1485, 1350, 1330, 1280, 1210, 1120, 1095, 1085, 905, 830, 780, 740, 700 | 1.15(t,J=7Hz,3H),2.37(s,3H),3.63 (t,J=5Hz,2H),4.1(q,J=7Hz,2H),4.2 (t,J=5Hz,2H),4.52(s,2H),4.98(d,J= 12Hz,1H),5.13(d,J=12Hz,1H),5.13 (s,1H),6.72(s,2H),7.4(s,5H),7.5- 8.3(m,4H),9.11(s,1H) |
| I-26 | 3-NO$_2$-C$_6$H$_4$ dihydropyridine with C$_3$H$_7$OCH$_2$CH$_2$OOC— and —COOCH$_2$CH$_2$OC$_3$H$_7$, CH$_3$ and —CH$_2$O—CONH$_2$ substituents | 17.3 g 62.8% | 91-99 | 236 355 | 3510, 3400, 3330, 2960, 2870, 1740, 1695, 1665, 1525, 1475, 1345, 1325, 1275, 1220, 1200, 1120, 1090, 1070, 1015, 905, 830, 785, 755, 710 | 0.82(t,J=7Hz,6H),1.46(m,4H), 2.34(s,3H),3.28(t,J=7Hz,4H),3.5 (t,J=5Hz,4H),4.08(t,J=5Hz,4H), 4.9(d,J=12Hz,1H),5.1(d,J=12Hz,1H), 5.12(s,1H),6.6(s,2H),7.35-8.2 (m,4H),8.95(s,1H) |
| I-27 | 3-NO$_2$-C$_6$H$_4$ dihydropyridine with CH$_3$OCH$_2$CH$_2$OOC— and —COOCH$_2$CH$_2$OCH$_3$, CH$_3$ and —CH$_2$O—CONH$_2$ substituents | 13.8 g 56% | 110-115 | 236 355 | 3500, 3400, 3000, 1690, 1640, 1610, 1530, 1485, 1350, 1330, 1280, 1210, 1110, 1095, 905, 830, 780, 755, 720 | 2.38(s,3H),3.3(s,6H),3.53(t,J= 5Hz,4H),4.12(t,J=5Hz,4H),5.05(d,J= 13Hz,1H),5.1(s,1H),5.15(d,J=13Hz, 1H),6.7(s,2H),7.5-8.3(m,4H), 9.1(s,1H) |

TABLE I-5-continued

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-28 | 4-(2-NO$_2$-C$_6$H$_4$)-3-COOC$_2$H$_5$-5-COOCH$_2$CH$_2$OC$_3$H$_7$-2-CH$_2$O-CONH$_2$-6-CH$_3$-1,4-dihydropyridine | 11.1 g 45% | 120–126 | 234 340 | 3400, 2970, 1710, 1690, 1640, 1605, 1530, 1490, 1335, 1320, 1280, 1205, 1110, 1100, 1080, 860, 830, 780, 755, 710 | 0.78(t,J=7Hz,3H),1.08(t,J=8Hz, 3H),1.4(m,2H),2.28(s,3H),3.23(t,J=7Hz, 2H),3.47(t,J=8Hz,2H),4.02(q,J=8Hz, 2H),4.05(t,J=8Hz,2H),4.83(d,J=13Hz, 1H),5.0(d,J=13Hz,1H), 5.63(s,1H), 6.6(br.s,2H),7.2–7.9(m,4H),8.86 (s,1H) |
| I-29 | 4-(4-NO$_2$-C$_6$H$_4$)-3-COOC$_2$H$_5$-5-COOCH$_2$CH$_2$OC$_3$H$_7$-2-CH$_2$O-CONH$_2$-6-CH$_3$-1,4-dihydropyridine | 11.6 g 47% | 117–121 | 233 280 370 | 3500, 3400, 3000, 1690, 1640, 1610, 1530, 1485, 1350, 1330, 1280, 1210, 1110, 1095, 905, 830, 780, 755, 720 | 0.85(t,J=8Hz,3H),1.15(t,J=8Hz, 3H),1.5(m,2H),2.38(s,3H),3.36(t,J= 8Hz,2H),3.55(t,J=4Hz,2H),4.03 (q,J=8Hz,2H),4.15(t,J=4Hz,2H),4.9 (d,J=12Hz,1H),5.02(s,1H), 5.05 (d,J=12Hz,1H),6.6(s,2H),7.42(d,J=9Hz, 2H),8.1(d,J=9Hz,2H),8.94(s,1H) |
| I-30 | 4-(2-CN-C$_6$H$_4$)-3-COOCH$_2$CH$_2$OCH$_3$-5-COOCH$_2$CH$_2$OCH$_3$-2-CH$_2$O-CONH$_2$-6-CH$_3$-1,4-dihydropyridine | 8.3 g 35% | 162–166 | 235 365 | 3540, 3380, 3000, 2230, 1710, 1690, 1640, 1605, 1490, 1390, 1335, 1275, 1200, 1120, 1090, 1040, 940, 840, 775 | 2.36,(s,3H),3.28(s,6H),3.53(t,J= 4Hz,4H),4.18(t,J=4Hz,4H),4.97(d,J= 13Hz,1H),5.13(d,J=13Hz,1H),5.25 (s,1H),6.73(br.s,2H),7.3–7.9(m,5H), 8.97(s,1H) |

TABLE I-5-continued

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-31 | [structure: 4-(2-methoxyphenyl) dihydropyridine with COOCH$_2$CH$_2$OCH$_3$, CH$_3$OCH$_2$CH$_2$OOC, CH$_3$, CH$_2$O—CONH$_2$ substituents] | 12.4 g 52% | — | 235 355 | 3420, 3350, 2980, 1720, 1680, 1605, 1490, 1380, 1320, 1280, 1210, 1110, 1095, 860, 750 | 2.26(s,3H),3.27(s,6H),3.5(t,J= 4Hz,4H),3.7(s,3H),4.08(t,J=4Hz, 4H),4.88(d,J=12Hz,1H),5.02(d,J= 12Hz,1H),5.2(s,1H),6.58(s,2H), 6.7–7.3(m,5H),8.57(s,1H) |
| I-32 | [structure: 4-(2-chlorophenyl) dihydropyridine with COOCH$_2$CH$_2$OCH$_3$, CH$_3$OCH$_2$CH$_2$OOC, CH$_3$, CH$_2$O—CONH$_2$ substituents] | 14.0 g 58% | 122–128 | 237 357 | 3420, 2980, 1705, 1685, 1640, 1605, 1490, 1385, 1370, 1330, 1280, 1205, 1110, 1100, 1080, 1040, 830, 755 | 2.31(s,3H),3.28(s,6H),3.52(t,J= 4Hz,4H),4.13(t,J=4Hz,4H),4.9 (d,J=13Hz,1H),5.1(d,J=13Hz,1H), 5.38(s,1H),6.7(br.s,2H),7.1–7.6 (m,5H),8.85(s,1H) |

EXAMPLE I-33

Preparation of 2-N-methylcarbamoyloxymethyl-6-methyl-4-(m-nitrophenyl)-3-ethoxycarbonyl-5-(β-ethoxyethoxy)carbonyl-1,4-dihydropyridine 10.1 g (50 millimoles) of ethyl 4-N-methylcarbamoyloxy-3-aminocrotonate and 15.4 g (50 millimoles) of β-ethoxyethyl 2-(m-nitrobenzylidene)acetoacetate were dissolved in 200 ml of n-propanol and reacted at a temperature of from 65° to 75° C. for 20 hours under stirring. The reaction mixture was concentrated under reduced pressure. The residue was crystallized from diisopropylether-hexane, whereby 11.1 g (yield: 45%) of 2-N-methylcarbamoyloxymethyl-6-methyl-4-(m-nitrophenyl)-3-ethoxycarbonyl-5-(β-ethoxyethoxy)carbonyl-1,4-dihydropyridine in crystal form was obtained.

mp: 148°-149° C.

UV: $\lambda_{max}^{MeOH}$ 236, 355 nm.

IR (KBr): 3390, 3280, 2980, 1680, 1640, 1610, 1535, 1480, 1355, 1280, 1205, 1120, 1095, 905, 830, 780, 760, 715 cm$^{-1}$.

NMR (90 MHz, DMSO-d$_6$): δ1.11 (t, J=8 Hz, 3H), 1.19 (t, J=7H, 3H), 2.39 (s, 3H), 2.67 (d, J=4.5 Hz, 3H), 3.48 (q, J=8 Hz, 2H), 3.65 (t, J=5 Hz, 2H), 4.12 (q, J=7 Hz, 2H), 4.15 (t, J=5 Hz, 2H), 5.06 (d, J=12 Hz, 1H), 5.14 (s, 1H), 5.18 (d, J=12 Hz, 1H), 7.22 (m, 1H), 7.6-8.25 (m, 4H), 9.18 (s, 1H).

EXAMPLE I-34 to I-42

In the same manner as in Example I-33, the compounds identified in Table I-6 were prepared.

TABLE I-6

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-34 | [3-NO$_2$-C$_6$H$_4$ dihydropyridine with C$_3$H$_7$OCH$_2$CH$_2$OOC, COOC$_2$H$_5$, CH$_3$, CH$_2$O—CONH—CH$_3$] | 6.8 g 37% | 136–137 | 236 355 | 3380, 3290, 2970, 1680, 1640, 1610, 1530, 1480, 1350, 1275, 1200, 1120, 1100, 905, 830, 780, 760, 715 | 0.82(t,J=8Hz,3H),1.13(t,J=8Hz, 3H),1.48(m,2H),2.35(s,3H),2.63 (d,J=6Hz,3H),3.33(t,J=8Hz,2H), 3.54(t,J=5Hz,2H),4.07(q,J=8Hz, 2H),4.11(t,J=5Hz,2H),5.0(d,J=13Hz, 1H), 5.09(s,1H),5.13(d,J=13Hz,1H), 7.15(m,1H),7.5–8.3(m,4H),9.10 (s,1H) |
| I-35 | [3-NO$_2$-C$_6$H$_4$ dihydropyridine with i-C$_3$H$_7$OCH$_2$CH$_2$OOC, COOC$_2$H$_5$, CH$_3$, CH$_2$O—CONH—CH$_3$] | 11.4 g 45% | 120–122 | 235 355 | 3370, 2980, 1680, 1640, 1610, 1530, 1480, 1350, 1275, 1205, 1120, 1095, 905, 830, 780, 760, 710 | 1.06(d,J=7Hz,6H),1.16(t,J=8Hz, 3H),2.37(s,3H),2.65(d,J=6Hz,3H), 3.56(m,1H),3.60(t,J=7Hz,2H),4.09(q,J= 8Hz,2H),4.10(t,J=7Hz,2H),5.03(d,J= 13Hz,1H), 5.11(s,1H),5.14(d,J=13Hz, 1H),7.16(m,1H),7.5–8.3(m,4H),9.12 (s,1H) |
| I-36 | [3-NO$_2$-C$_6$H$_4$ dihydropyridine with C$_2$H$_5$OOC, COOCH$_2$CH$_2$OCH$_3$, CH$_3$, CH$_2$O—CONH—CH$_3$] | 11.9 g 50% | 152–156 | 235 355 | 3370, 3280, 2980, 1680, 1640, 1610, 1530, 1480, 1350, 1275, 1205, 1100, 905, 830, 780, 760, 715 | 1.17(t,J=7Hz,3H),2.37(s,3H), 2.65(d,J=5Hz,3H),3.27(s,3H),3.52 (t,J=5Hz,2H),4.10(q,J=7Hz,2H), 4.16(t,J=5Hz,2H),5.06(d,J=14Hz,1H), 5.1(s,1H),5.14(t,J=14Hz,1H),7.18 (m,1H),7.5–8.3(m,4H),9.12(s,1H) |

TABLE I-6-continued

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-37 | [3-NO$_2$-C$_6$H$_4$ dihydropyridine with COOCH$_2$CH$_2$OC$_3$H$_7$, C$_2$H$_5$OOC, CH$_3$, CH$_2$O—CONH—CH$_3$] | 12.9 g 51% | 152–155.5 | 236 355 | 3380, 2980, 1680, 1640, 1610, 1530, 1485, 1355, 1280, 1205, 1100, 910, 830, 780, 760, 715 | 0.86(t,J=7Hz,3H),1.2(t,J=7Hz,3H),1.52(m,2H),2.4(s,3H),2.68(d,J=6Hz,3H),3.38(t,J=7Hz,2H),3.58(t,J=4Hz,2H),4.1(q,J=7Hz,2H),4.18(t,J=4Hz,2H),5.09(d,J=13Hz,1H),5.13(s,1H),5.18(d,J=13Hz,1H),7.2(m,1H),7.4–8.4(m,4H),9.12(s,1H) |
| I-38 | [3-NO$_2$-C$_6$H$_4$ dihydropyridine with COOCH$_2$CH$_2$OC$_3$H$_7$, C$_3$H$_7$OCH$_2$CH$_2$OOC, CH$_3$, CH$_2$O—CONH—CH$_3$] | 17.2 g 61% | 119–120 | 236 355 | 3350, 3300, 2960, 2870, 1685, 1635, 1600, 1530, 1480, 1350, 1275, 1250, 1200, 1130, 1100, 1015, 990, 900, 830, 780, 760, 750, 710 | 0.83(t,J=7Hz,6H),1.5(m,4H),2.35(s,3H),2.62(d,J=5Hz,3H),3.3(t,J=7Hz,4H),3.52(t,J=4Hz,4H),4.12(t,J=4Hz,4H),5.0(d,J=13Hz,1H),5.1(d,J=13Hz,1H),5.14(s,1H),7.1(m,1H),7.4–8.3(m,4H),9.0(s,1H) |
| I-39 | [3-NO$_2$-C$_6$H$_4$ dihydropyridine with COOCH$_2$CH$_2$OCH$_3$, C$_2$H$_5$OOC, CH$_3$, CH$_2$O—CONH—cyclohexyl] 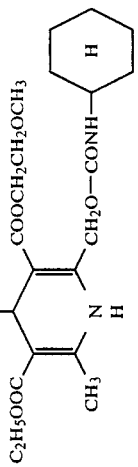 | 16.6 g 61% | 148–152 | 235 355 | 3350, 2950, 1680, 1640, 1610, 1530, 1480, 1350, 1310, 1210, 1095, 1060, 900, 830, 780, 740, 710 | 1.18(t,J=8Hz,3H),1.7(br.s,10H),2.37(s,3H),3.25(s,3H),3.35(m,1H),3.5(t,J=4Hz,2H),4.08(q,J=8Hz,2H),4.15(t,J=4Hz,2H),5.05(d,J=13Hz,1H),5.1(s,1H),5.15(d,J=13Hz,1H),7.25(d,J=7Hz,1H),7.5–8.3(m,4H),9.1(s,1H) |

TABLE 1-6-continued

| Example No. | Compounds (I) | Yield | Melting Point °C. | UV $\lambda_{max}^{MeOH}$ nm | IR(KBr): cm$^{-1}$ | $^1$H NMR (90 MHz, DMSO-d$_6$): δ in ppm |
|---|---|---|---|---|---|---|
| I-40 | [structure: 3-NO$_2$-phenyl dihydropyridine with COOC$_2$H$_5$, C$_2$H$_5$OCH$_2$CH$_2$OOC, CH$_3$, CH$_2$O—CONH-phenyl] | 13.6 g 49% | 138–142 | 238 356 | 3350, 3000, 1685, 1645, 1600, 1530, 1480, 1350, 1310, 1205, 1100, 1080, 1070, 905, 850, 825, 770, 740, 710, 690 | 1.1(t,J=7Hz,3H),1.2(t,J=7Hz,3H), 2.4(s,3H),3.5(q,J=7Hz,2H),3.65(t,J=5Hz,2H),4.1(q,J=7Hz,2H),4.15(t,J=5Hz,2H),5.05(d,J=12Hz,1H),5.15(s,1H), 5.2,(d,J=12Hz,1H),7.0-8.3(m,9H), 9.27(s,1H),9.86(s,1H) |
| I-41 | [structure: 3-NO$_2$-phenyl dihydropyridine with COOCH$_2$CH$_2$OC$_3$H$_7$, C$_3$H$_7$OCH$_2$CH$_2$OOC, CH$_3$, CH$_2$O—CONH-(4-Cl-phenyl)] | 15.5 g 47% | 140–145 | 242 357 | 3400, 3000, 1700, 1600, 1530, 1490, 1480, 1350, 1280, 1220, 1100, 1070, 1030, 900, 825, 770, 740, 705 | 0.85(t,J=7Hz,6H),1.5(m,4H),2.4 (s,3H),3,37(t,J=7Hz,4H),3.6(t,J=4Hz, 4H),4.18(t,J=4Hz,4H),5.15(s,1H),5.15 (d,J=12Hz,1H),5.34(d,J=12Hz,1H),7.43 (,d,J=9Hz,2H),7.63(d,J=9Hz,2H),7.5– 8.3(m,5H),9.15(s,1H) |
| I-42 | [structure: 3-NO$_2$-phenyl dihydropyridine with COOCH$_2$CH$_2$OCH$_3$, C$_3$H$_5$OCH$_2$CH$_2$OOC, CH$_3$, CH$_2$O—CONH-(3,4-diCl-phenyl)] | 13.9 g 40% | 128–135 | 243 355 | 3420, 3300, 3100, 3000, 1750, 1690, 1670, 1610, 1595, 1530, 1480, 1350, 1290, 1220, 1120, 1100, 910, 810, 755, 710 | 0.85(t,J=7Hz,6H),1.5(m,4H),2.4 (s,3H),3.38(t,J=7Hz,4H), 3.58(t,J= 4Hz,4H),4.18(t,J=4Hz,4H),5.04 (s,1H),5.05(d,J=12Hz,1H),5.25(d,J= 12Hz,1H),7.3–8.2(m,8H),9.2(s,1H) |

EXAMPLE I-43

Preparation of 2-carbamoyloxymethyl-6-methyl-4-(m-nitrophenyl)-3-methoxycarbonyl-5-[β-(N-methylbenzylamino)ethoxy]carbonyl-1,4-dihydropyridine 8.7 g (50 millimoles) of methyl 4-carbamoyloxy-3-aminocrotonate and 19.1 g (50 millimoles) of β-(N-methylbenzylamino)ethyl 2-(m-nitrobenzylidene)acetoacetate were dissolved in 300 ml of ethanol and reacted at a temperature of from 60° to 70° C. for 20 hours under stirring. The reaction mixture was concentrated under reduced pressure. The residue was separated and purified by silica gel column chromatography. By using ethylacetate as the developer solvent, the desired fraction was collected and concentrated under reduced pressure. The residue was dissolved in acetone. A hydrochloric acid-ethanol solution was added thereto. The precipitates thereby formed were collected and recrystallized from acetone-ethylacetate, whereby 9.2 g (yield: 32%) of 2-carbamoyloxymethyl-6-methyl-4-(m-nitrophenyl)-3-methoxy-carbonyl-5-[β-(N-methylbenzylamino)ethoxy]carbonyl-1,4-dihydropyridine hydrochloride in crystal form was obtained.

mp: 117.5°–121° C.

UV: $\lambda_{max}.^{MeOH}$ 236, 355 nm.

IR (KBr): 3400, 2950, 1720, 1690, 1640, 1610, 1525, 1475, 1350, 1320, 1210, 1010, 900, 825, 780, 740, 700 cm$^{-1}$.

NMR (90 MHz, DMSO-d$_6$): δ2.37 (s, 3H), 2.57 (s, 3H), 3.36 (m, 2H), 3.68 (s, 3H), 4.25 (s, 2H), 4.43 (m, 2H), 4.88 (d, J=14 Hz, 1H), 5.03 (d, J=14 Hz, 1H), 5.03 (s, 1H), 6.73 (br. s, 2H), 7.42 (s, 5H), 7.5–8.2 (m, 4H), 9.2 (s, 1H).

EXAMPLE I-44 to I-50

In the same manner as in Example I-43, the compounds identified in Table I-7 were prepared.

TABLE I-7

| Example No. | Compounds (I) | Yield | Melting Point °C. | UV $\lambda_{max}^{MeOH}$, nm |
|---|---|---|---|---|
| I-44 | (structure shown) ·HCl | 8.8 g 30% | 77–82 | 236 353 |
| I-45 | (structure shown) ·HCl | 11.7 g 34% | — | 236 353 |
| I-46 | (structure shown) ·HCl | 10.8 g 40% | 75–80 | 228 342 |
| I-47 | (structure shown) ·2HCl | 10.6 g 36% | 163–168 | 231 345 |

TABLE I-7-continued

| I-48 | (structure: morpholine-N-CH₂CH₂OOC- / COOCH₃ / 3-NO₂-phenyl / CH₃ / CH₂O—CONH₂ · HCl) | 11.6 g 43% | 68–75 | 235 355 |

| Example No. | IR(KBr): cm⁻¹ | ¹H NMR (90 MHz, DMSO-d₆): δ in ppm |
|---|---|---|
| I-44 | 3380, 3330, 2960, 1690, 1640, 1605, 1530, 1480, 1350, 1280, 1250, 1210, 1105, 1050, 905, 830, 780, 740, 700 | 2.13(s,3H),2.36(s,3H),2.6(t,J=6Hz,2H),2.65(d,J=5Hz,3H),3.5(s,2H),3.62(s,3H),4.16(t,J=6Hz,2H),5.1(d,J=13Hz,1H),5.13(s,1H),5.16(d,J=13Hz,1H),7.2(m,1H),7.33(s,5H),7.4–8.3(m,4H),9.16(s,1H) |
| I-45 | 3400, 3320, 2960, 1740 1690, 1640, 1605, 1530, 1480, 1350, 1280, 1250, 1210, 1100, 905, 830, 780, 750, 720 | 2.13(s,3H),2.36(s,3H),2.6(t,J=6Hz,2H),3.5(s,2H),3.62(s,3H),4.16(t,J=6Hz,2H),5.13(s,1H),5.13(d,J=12Hz,1H),5.33(d,J=12Hz,1H),7.3–8.3(m,9H),7.33(s,5H),9.2(s,1H) |
| I-46 | 3400, 2950, 1740, 1685 1525, 1500, 1350, 1245, 1200, 1190, 1090, 1020, 1010, 975, 900, 825, 800, 760, 730, 690 | 1.7(br.s,6H),2.46(s,3H),2.8(br.s,4H),3.3(s,3H),3.3(m,2H),4.35(m,2H),4.9(s,2H),5.05(s,1H),5.25(br.s,2H),7.5–8.3(m,4H),9.35(s,1H) |
| I-47 | 3420, 1690, 1525, 1500, 1350, 1210, 1095, 1010, 975, 900, 830, 800, 780, 760, 740 | 2.48(s,3H),2.9(s,3H),3.3–4.0(br.s,10H),3.7(s,3H),4.5(m,2H),5.02(d,J=12Hz,1H),5.15(s,1H),5.2(d,J=12Hz,1H),6.8(br.s,2H),7.6–8.3(m,4H),9.38(s,1H) |
| I-48 | 3450, 2960, 1690, 1640, 1610, 1530, 1480, 1350, 1330, 1280, 1210, 1100, 1070, 1020, 910, 830, 780, 760, 710 | 2.45,(s,3H),2.9–4.1(m,10H),3.68(s,3H),4.5(m,2H),4.97(d,J=13Hz,1H),5.12(s,1H),5.14(d,J=13Hz,1H),6.73(br.s,2H),7.5–8.3(m,4H),9.35(s,1H) |

| Example No. | Compounds (I) | Yield | Melting Point °C. | UV $\lambda_{max}^{MeOH}$, nm |
|---|---|---|---|---|
| I-49 | (structure: (C₂H₅)₂NCH₂CH₂OOC- / COOCH₃ / 3-NO₂-phenyl / CH₃ / CH₂O—CONH₂ · HCl) | 8.7 g 33% | — | 230 345 |
| I-50 | (structure: C₆H₅CH₂(CH₃)NCH₂CH₂OOC- / COOCH₂CH₂OC₃H₇ / 3-NO₂-phenyl / CH₃ / CH₂O—CONH₂ · HCl) | 13.3 g 41% | 71–72 | 235 355 |

| Example No. | IR(KBr): cm⁻¹ | ¹H NMR (90 Hz, DMSO-d₆): δ in ppm |
|---|---|---|
| I-49 | 3420, 2950, 1735, 1685, 1525, 1500, 1350, 1240, 1200, 1190, 1090, 1020, 975, 900, 825, 800, 760, 730, 690 | 1.19(m,6H),2.45(s,3H),3.06(m,4H),3.25(t,J=7Hz,2H),3.55(s,3H),4.36(t,J=7Hz,2H),4.93(s,2H),5.08(s,1H),6.75(br.s,2H),7.5–8.3(m,4H),9.4(br.s,1H) |
| I-50 | 3420, 2960, 1690, 1640, 1610, 1530, 1480, 1350, 1320, 1280, 1210, 1080, 900, 830, 810, 780, 740, 700 | 0.8(t,J=8Hz,3H),1.46(m,2H),2.4(s,3H),2.6(s,3H),3.48(t,J=8Hz,2H),3.52(m,2H),3.68(m,2H),4.12(m,2H),4.26(br.s,2H),4.44(m,2H),4.88(d,J=13Hz,1H),5.03(s,1H),5.08(d,J=13Hz,1H),6.65(br.s,2H), |

7.43(s,5H),7.5–8.2(m,4H),9.2(s,1H)

EXAMPLE I-51
Preparation of 2-N-methylcarbomoyloxymethyl-6-methyl-4-(m-nitrophenyl)-3,5-diethoxycarbonyl-1,4-dihydropyridine 10.1 g (50 millimoles) of ethyl 4-N-methylcarbamoyloxy-3-aminocrotonate, 7.6 g (50 millimoes) of m-nitrobenzaldehyde and 6.5 g (50 millimoles) of ethyl acetoacetate were dissolved in 200 ml of ethanol and reacted at a temperature of from 60° to 70° C. for 16 hours under stirring. The reaction mixture was concentrated under reduced pressure. The residue was crystallized from diisopropylether, whereby 7.6 g (yield: 34%) of 2-N-methylcarbamoyloxymethyl-6-methyl-4-(m-nitrophenyl)-3,5-diethoxycarbonyl-1,4-dihydropyridine in crystal form was obtained.

mp: 192°–193° C.

The analytical data of this product by UV, IR and NMR agreed very well to the data obtained with respect to the product of Example I-8.

EXAMPLE I-52
Preparation of 2-N-methylcarbamoyloxymethyl-6-methyl-4-(m-nitrophenyl)-3,5-diethoxycarbonyl-1,4-dihydropyridine 9.2 g (50 millimoles) of ethyl 4-N-methylcarbamoyloxy-2-butynoate, 13.2 g (50 millimoles) of ethyl 2-(m-nitrobenzylidene)acetoacetate and 10 g (125 millimoles) of ammonium acetate were dissolved in 200 ml of ethanol and reacted at a temperature of from 60° to 70° C. for 16 hours. The reaction mixture was concentrated under reduced pressure. The oily residue was extracted with 200 ml of ethylacetate. The ethylacetate extraction solution was dried over anhydrous magnesium sulfate and then concentrated under reduced pressure. The residue was separated and purified by means of a liquid chromatography apparatus (System 500 A manufactured by Waters Co.) by using a Prep PAK-500/silica column and ethylacetate-hexane (2:1) as the developer solvent. The desired fraction was collected and concentrated under reduced pressure. The residue was crystallized from diisopropylether, whereby 4.8 g (yield: 21.5%) of 2-N-methylcarbamoyloxymethyl-6-methyl-4-(m-nitrophenyl)-3,5-diethoxycarbonyl-1,4-dihydropyridine in crystal form was obtained.

mp: 192°–193° C.

The analytical data of this product by UV, IR and NMR agreed very well to the data with respect to the product of Example I-8.

EXAMPLE I-53
Preparation of 2-N-methylcarbamoyloxymethyl-6-methyl-4-(m-nitrophenyl)-3,5-diethoxycarbonyl-1,4-dihydropyridine 9.2 g (50 millimoles) of ethyl 4-N-methylcarbamoyloxy-2-butynoate, 7.5 g (50 millimoles) of m-nitrobenzaldehyde, 6.4 g (50 millimoles) of ethylacetoacetate and 10 g (125 millimoles) of ammoniumacetate were dissolved in 200 ml of ethanol and reacted at a temperature of from 60° to 70° C. for 16 hours under stirring. The reaction mixture was concentrated under reduced pressure. The residue was extracted with 200 ml of ethylacetate. The extraction solution was dried over anhydrous magnesium sulfate and then concentrated under reduced pressure. The residue was separated and purified by means of a liquid chromatography apparatus (System 500 A manufactured by Waters Co.) by using a Prep PAK-500/silica column and ethylacetatehexane (2:2) as the developer solvent. The desired fraction was collected and concentrated under reduced pressure. The residue thereby obtained was crystallized from diisopropylether, whereby 5.0 g (yield: 22.3%) of 2-N-methylcarbamoyloxymethyl-6-methyl-4-(m-nitrophenyl)-3,5-diethoxycarbonyl-1,4-dihydropyridine in crystal form was obtained.

mp: 192°–193° C.

The analytical data of this product by UV, IR and NMR agreed very well to the data obtained with respect to the product of Example I-8.

We claim:

1. A 3-carbamoyloxyalkylpropiolic acid derivative represented by the general formula:

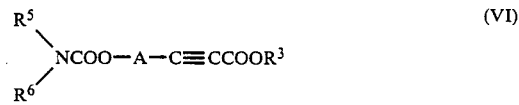

(VI)

where $R^3$ is lower alkyl, mono-, di- or tri-halo-$C_{1-4}$-alkyl, lower alkenyl, lower alkynyl, $C_{7-8}$-aralkyl, $C_{6-10}$-aryl, mono- or di-hydroxy-$C_{2-4}$-alkyl, lower alkoxy-$C_{2-4}$-alkyl, lower alkenyloxy-$C_{2-3}$-alkyl, $C_{7-8}$-aralkyloxy-$C_2$-alkyl, $C_6$-aryloxy-$C_{2-4}$-alkyl, pyridyl, quinolyl, pyridyloxy-$C_{2-6}$ alkyl or

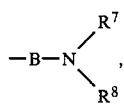

where B is straight-chained or branched $C_{2-4}$-alkylene, and each of $R^7$ and $R^8$ is lower alkyl, $C_7$-aralkyl or $C_{6-10}$-aryl, or $R^7$ and $R^8$ form, together with the adjacent nitrogen atom, piperidino, 1-piperazinyl, 1-(4-methylpiperazinyl), 1-(4-ethylpiperazinyl), 1-(4-propylpiperazinyl), 1-(4-methylhomopiperazinyl), morpholino, homomorpholinyl, 1-pyrrolidinyl, 1-imidazolidinyl, 1-imidazolinyl, 1-pyrazolidinyl or 1-indolinyl group, A is $C_{1-8}$-alkylene or phenyl substituted $C_{1-8}$ alkylene, and each of $R^5$ and $R^6$ is hydrogen, lower alkyl, mono-, di- or tri-halo-$C_{1-4}$-alkyl, hydroxy-$C_{2-4}$-alkyl, $C_{3-7}$-cycloalkyl, pyridyl, $C_{7-8}$-aralkyl, or $C_{6-10}$-aryl, or $R^5$ or $R^6$ form, together with the adjacent nitrogen atom, piperidino, 1-piperazinyl, 1-(4-methylpiperazinyl), 1-(4-ethylpiperazinyl), 1-(4-propylpiperazinyl), 1-(4-methylhomopiperazinyl), morpholino, homomorpholinyl, 1-pyrrolidinyl, 1-imidazolidinyl, 1-imidazolinyl, 1-pyrazolidinyl or 1-indolinyl group.

2. The 3-carbamoyloxyalkylpropiolic acid derivative according to claim 1, wherein $R^3$ is methyl, ethyl, propyl, isopropyl, butyl, isobutyl, tertiary butyl, pentyl, hexyl, β-chloroethyl, β-bromoethyl, β-chloropropyl, γ-chloropropyl, ω-chlorobutyl, β,β-dichloroethyl, trifluoromethyl, β,β,β-trichloroethyl, vinyl, allyl, 3-butenyl, isopropenyl, propargyl, 2-butynyl, benzyl, α-methylbenzyl, phenethyl, phenyl, pyridyl, naphthyl, quinolyl, β-hydroxyethyl, β-hydroxypropyl, β-hydroxybutyl, γ-hydroxypropyl, ω-hydroxybutyl, β,γ-dihydroxypropyl, β-methoxyethyl, β-ethoxyethyl, β-propoxyethyl, β-isopropoxyethyl, β-butoxyethyl, β-isobutoxyethyl, β-tertiarybutoxyethyl, β-methoxypropyl, β-ethoxypropyl, β-propoxypropyl, β-isopropoxypropyl, β-butoxypropyl, γ-methoxypropyl, γ-ethoxypropyl, γ-propoxypropyl, γ-butoxypropyl, ω-propoxybutyl, β-vinyloxyethyl, β-allyloxyethyl, β-(3-butenyloxy)ethyl, β-isopropenyloxyethyl, β-allyloxypropyl, β-benzyloxyethyl, β-phenethyloxyethyl, β(α-methylbenzyloxy)ethyl, β-phenoxyethyl, β-pyridyloxyethyl, β-phenoxypropyl, β-phenoxybutyl, β-dimethylaminoethyl, β-diethylaminoethyl, β-methylethylaminoethyl, β-dimethylaminopropyl, γ-dimethylaminopropyl, ω-dimethylaminobutyl, β-N-methylbenzylaminobutyl, β-N-methylbenzylaminopropyl, β-N-methylbenzylaminobutyl, γ-N-methylbenzylaminopropyl, ω-N-methylbenzylaminobutyl, β-piperidinoethyl, β-(4-methylpiperazinyl)ethyl, β-(4-ethylpiperazinyl)ethyl, β-(4-propylpiperazinyl)ethyl, β-(4-methylhomopiperazinyl)ethyl, β-morpholinoethyl, γ-morpholinopropyl, ω-morpholinobutyl, β-homomorpholinyl)ethyl, β-(1-pyrrolidinyl)ethyl, β-(1-imidazolidinyl)ethyl, β-(1-imidazolinyl)ethyl, β-(1-pyrazolidinyl)ethyl, β-(1-indolinyl)ethyl or β-N-methylanilinoethyl; A is methylene, methylmethylene, ethylmethylene, phenylmethylene, dimethylmethylene, methylethylmethylene, methylisobutylmethylene, benzylmethylene, benzylethylene, methylethylene, ethylethylene, trimethylene or tetramethylene; and each of $R^5$ and $R^6$ is selected from the group consisting of hydrogen, methyl, ethyl, propyl, isopropyl, butyl, isobutyl, tertiarybutyl, β-chloroethyl, β-bromoethyl, β-chloropropyl, γ-chloropropyl, ω-chlorobutyl, β,β-dichloroethyl, β,β,β-trichloroethyl, trifluoromethyl, β-hydroxyethyl, β-hydroxypropyl, γ-hydroxypropyl, ω-hydroxybutyl, cyclopropyl, cyclobutyl, cyclopentyl, cyclohexyl, cycloheptyl, benzyl, α-methylbenzyl, phenethyl, phenyl, pyridyl and naphthyl, or $R^5$ and $R^6$ form, together with the adjacent nitrogen atom, a heterocyclic group selected from the group consisting of piperidino, 4-methylpiperazinyl, 4-ethylpiperazinyl, 4-propylpiperazinyl, 4-methylhomopiperazinyl, morpholino, homomorpholinyl, 1-pyrrolidinyl, 1-imidazolidinyl, 1-imadizolinyl, 1-pyrazolidinyl and 1-indolinyl.

3. The 3-carbamoyloxyalkylpropiolic acid derivative according to claim 1, wherein $R^3$ is methyl, ethyl, propyl, isopropyl, butyl, isobutyl, β-chloroethyl, allyl, propargyl, benzyl, phenyl, β-methoxyethyl, β-propoxyethyl, β-isopropoxyethyl, β-allyloxyethyl, β-benzyloxyethyl, β-phenoxyethyl, β-N-methylbenzylaminoethyl, β-piperidinoethyl, β-(4-methylpiperazino)ethyl or β-morpholinoethyl, each of $R^5$ and $R^6$ is hydrogen, methyl, ethyl, propyl, isopropyl, butyl, isobutyl, tertiary butyl, β-chloroethyl, benzyl, phenyl, p-chlorophenyl, β-hydroxyethyl or cyclohexyl, or $R^5$ and $R^6$ form, together with the adjacent nitrogen atom a heterocyclic group selected from the group consisting of piperidino, 4-methylpiperazino and morpholino and A is methylene, ethylene, methyl methylene or dimethyl methylene.

4. The 3-carbamoyloxyalkylpropiolic acid derivative according to claim 1, which is β-methoxyethyl 4-carbamoyloxy-2-butynoate, methyl 4-N-methylcarbamoyloxy-2-butynoate, ethyl 4-N-methylcarbamoyloxy-2-butynoate, β-methoxyethyl 4-N-methylcarbamoyloxy-2-butynoate, ethyl 4-N-ethylcarbamoyloxy-2-butynoate, ethyl 4-N-propylcarbamoyloxy-2-butynoate, ethyl 4-N-t-butylcarbamoyloxy-2-butynoate, ethyl 4-N-cyclohexylcarbamoyloxy-2-butynoate, ethyl 4-N-phenylcarbamoyloxy-2-butynoate, methyl 4-N-(p-chlorophenyl)carbamoyloxy-2-butynoate, β-propoxyethyl 4-N,N-dmethylcarbamoyloxy-2-butynoate, ethyl 4-N,N-dicyclohexylcarbamoyloxy-2-butynoate, ethyl 4-N,N-diphenylcarbamoyloxy-2-butynoate, ethyl 4-piperidinocarbonyloxy-2-butynoate, ethyl 4-(4-methylpiperazino)carbonyloxy-2-butynoate, ethyl 4-morpholinocarbonyloxy-2-butynoate, ethyl 4-N,N-bis(β-chloroethyl)carbonyloxy-2-butynoate or ethyl 4-N-benzyl-N-methylcarbamoyloxy-2-butynoate.

5. The 3-carbamoyloxyalkylpropiolic acid derivative according to claim 1, which is ethyl 4-carbamoyloxy-2-butynoate, isobutyl 4-carbamoyloxy-2-butynoate, β-propoxyethyl 4-carbamoyloxy-2-butynoate or β-propoxyethyl 4-N-methylcarbamoyloxy-2-butynoate.

6. The 3-carbamoyloxyalkylpropiolic acid derivative according to claim 1, which is methyl 4-carbamoyloxy-2-butynoate.

7. The 3-carbamoyloxyalkylpropiolic acid derivative according to claim 1, which is isopropyl 4-carbamoyloxy-2-butynoate.

* * * * *